(12) United States Patent
Kydonieus

(10) Patent No.: US 8,992,977 B2
(45) Date of Patent: Mar. 31, 2015

(54) MULTI-DAY DELIVERY OF BIOLOGICALLY ACTIVE SUBSTANCES

(75) Inventor: Agis Kydonieus, Kendall Park, NJ (US)

(73) Assignee: Samos Pharmaceuticals, LLC, Kendall Park, NJ (US)

( * ) Notice: Subject to any disclaimer, the term of this patent is extended or adjusted under 35 U.S.C. 154(b) by 989 days.

(21) Appl. No.: 12/665,977

(22) PCT Filed: Jun. 26, 2008

(86) PCT No.: PCT/US2008/007983
§ 371 (c)(1),
(2), (4) Date: Nov. 8, 2010

(87) PCT Pub. No.: WO2009/002542
PCT Pub. Date: Dec. 31, 2008

(65) Prior Publication Data
US 2011/0046599 A1 Feb. 24, 2011

Related U.S. Application Data

(60) Provisional application No. 60/937,604, filed on Jun. 27, 2007, provisional application No. 60/958,914, filed on Jul. 9, 2007, provisional application No. 60/959,298, filed on Jul. 12, 2007.

(51) Int. Cl.
*A61K 9/14* (2006.01)
*A61K 9/00* (2006.01)
*A61K 47/48* (2006.01)

(52) U.S. Cl.
CPC ............ *A61K 9/0019* (2013.01); *A61K 9/0021* (2013.01); *A61K 47/481* (2013.01); *A61K 47/48123* (2013.01); *A61K 9/0009* (2013.01); *A61K 9/0043* (2013.01)
USPC ...................................................... 424/484

(58) Field of Classification Search
USPC ...................................................... 424/484
See application file for complete search history.

(56) References Cited

U.S. PATENT DOCUMENTS

| | | | |
|---|---|---|---|
| 4,310,103 A | 1/1982 | Reilly et al. | |
| 5,545,721 A * | 8/1996 | Carroll et al. | 530/391.7 |
| 5,783,178 A * | 7/1998 | Kabanov et al. | 424/78.31 |
| 6,309,633 B1 * | 10/2001 | Ekwuribe et al. | 424/85.1 |
| 6,576,636 B2 * | 6/2003 | Webb et al. | 514/263.38 |
| 2003/0129193 A1 * | 7/2003 | Thorpe et al. | 424/155.1 |
| 2004/0180036 A1 * | 9/2004 | Ashton et al. | 424/85.1 |
| 2005/0209265 A1 * | 9/2005 | Briesewitz et al. | 514/291 |
| 2005/0255561 A1 * | 11/2005 | Tosi et al. | 435/69.7 |

FOREIGN PATENT DOCUMENTS

WO    WO 2006/030217 A2    3/2006

OTHER PUBLICATIONS

Burri, B.J., et al., "Serum carotenoid depletion follows first-order kinetics in healthy adult women fed naturally low carotenoid . . . ", J. Nutr., vol. 131, pp. 2096-2100 (2001).
Chen, H., et al., "Lectin-bearing polymerized liposomes as potential oral vaccine carriers", Pharm. Res., vol. 13, pp. 1378-1383 (1996).
Cohn, W., et al., "Comparative multiple dose plasma kinetics of lycopene administered in tomato juice, tomato soup or lycopene . . . ", Eur. J. Nutr. vol. 43, pp. 304-312 (2004).
Collard, W.T., et al., "Biodistribution, metabolism, and in vivo gene expression of low molecular weight glycopeptide . . . ", J. Pharm. Sci., vol. 89, pp. 499-512 (2000).
Freysz, L., et al., "Metabolism of brain sphingomyelins: Half-lives of sphingosine, fatty acids and phosphate from two types . . . ", J. Neurochem., vol. 27, pp. 335-359 (1976).
Greenwald, et al., "Effective drug delivery by PEGylated drug conjugates," Advanced Drug Delivery Reviews, vol. 55, pp. 217-250 (2003).
Imai, T., "Human carboxylesterase isozymes: catalytic properties and rational drug design", Drug Metab. Pharmacokinet., vol. 21, pp. 173-185 (2006).
Kunin, C.M., et al., "Antimicrobial activities of mefloquine and a series of related compounds", Antimicrob. Agents Chemother., vol. 44, pp. 848-852 (2000).
Minko, T., "Soluble polymer conjugates for drug delivery", Drug Discov. Today: Technologies, vol. 2, pp. 15-20 (2005).
Pawlosky, R.J., et al., "Physiological compartmental analysis of alpha-linolenic acid metabolism in adult humans", J. Lipid Res., vol. 42, pp. 1257-1265 (2001).
Rautio, J., et al., "Prodrugs: design and clinical applications", Nat. Rev. Drug Discov., vol. 7, pp. 255-270 (2008).
Rosen, H. and T. Abribat, "The rise and rise of drug delivery", Nat. Rev. Drug Discov., vol. 4, pp. 381-385 (2005).
Thanou, M.M., et al., "Effect of degree of quaternization of N-trimethyl chitosan chloride for enhanced transport . . . ", J. Control. Release, vol. 64, pp. 15-25 (2000).
Yoo, H.S., et al., "Biodegradable nanoparticles containing doxorubicin-PLGA conjugate for sustained release", Pharm. Res., vol. 16, pp. 1114-1118 (1999).
International Search Report and Written Opinion in International Application No. PCT/US2008/007983, mailed Oct. 14, 2008.

* cited by examiner

*Primary Examiner* — Ali Soroush
(74) *Attorney, Agent, or Firm* — Potter Anderson and Corroon, LLP

(57) ABSTRACT

Compositions and methods for modifying biologically active substances to achieve multi-day delivery of such substances, particularly through oral or parenteral administration, are disclosed. The compositions include the biologically active substance conjugated to a carrier having a suitably long half life, typically more than one day, wherein the conjugate optionally contains a spacer linking the carrier to the biologically active substance. Pharmaceutical formulations of the conjugates are also disclosed, as are methods of extending delivery of a single dose of a biologically active substance for more than one day.

10 Claims, 2 Drawing Sheets

MULTI-DAY DELIVERY OF BIOLOGICALLY ACTIVE SUBSTANCES

FIELD OF THE INVENTION

This invention relates to the field of controlled delivery of biologically active substances. In particular, the invention provides compositions and methods for modifying biologically active substances to achieve multi-day delivery of such substances, particularly through oral or parenteral administration.

BACKGROUND OF THE INVENTION

Various publications, including patents, published applications, technical articles and scholarly articles are cited throughout the specification. Each of these cited publications is incorporated by reference herein, in its entirety.

Oral delivery of biologically active substances a preferred way to administer drugs to humans. In general, other methods of delivery, such as nasal, transdermal, buccal, injectable and other, are only used for special situations and when oral delivery is not possible. However, oral delivery of drugs is subject to two limitations. First, pertaining particularly to oral delivery, drugs ingested are passed through the gastrointestinal tract within 24 hours and sometimes in a few hours after ingestion. The second limitation, which pertains to oral and parenteral delivery, is that the half life of most drugs is less than a day and usually no more than a few hours. Thus it is very difficult for a standard immediate release single oral dose of a drug to be effective for more than 24 hours and in most cases more than several hours. A standard immediate release formulation is one that is designed to release the drug immediately upon dissolution in the gastrointestinal tract. As a matter of fact, a whole industry has developed around controlled or extended release of drugs, with a major objective to extend the therapeutic life of drugs from a few hours to even one day. These extended release formulations use different technologies to slowly release the drug as it travels through the gastrointestinal tract. For example Elan, Depomed, Alza, Biovail, Pennwest and Kos Pharmaceuticals are some of the companies that have developed such technologies, based on polymer coatings, hydrogels, polymer foams, osmotic pressure, and other technologies (for a review, see Rosen, H. & T. Arbribat, 2005, *Nat. Rev. Drug Discovery*, published online Apr. 22, 2005, doi:10.1038/nrd1721). Other research has focused on the development of prodrugs designed to improve physicochemical, biopharmaceutical or pharmokinetic properties of drugs, including controlling or extending drug release in the body (for a review, see J. Rautio, et al., 2008, *Nat. Rev. Drug Discovery* Volume 7, March 2008, 255-270).

Notwithstanding the technical advances referred to above, a single dose of an immediate or extended release orally delivered formulation of a drug is almost never effective for more than a day, save a handful of drugs that have very long half lives. Thus, there is a need in the art to develop drug compositions and methods of manufacture that are able to extend the delivery of a single drug dose to beyond one day, and preferably to multiple days. This invention addresses those needs.

SUMMARY OF THE INVENTION

One aspect of the invention features a controlled release drug conjugate (CRDC) comprising a biologically active substance linked to a carrier, and optionally comprising a spacer that links the biologically active substance to the carrier, wherein the conjugate has a half life in a patient's body of more than one day. In one series of embodiments, the CRDC does not comprise a spacer, whereas in another series of embodiments, the CRDC comprises a spacer. In either series of embodiments, the CRDC may comprise more than one biologically active substance, one or more carrier and/or more than one spacer. In one embodiment the carrier itself, in addition to the CRDC as a whole, has a half life in a patient's body of more than one day.

In some forms of the CRDC, the biologically active substance is covalently linked to the carrier. The biologically active substance may be released from the carrier in the patient's body, or it may be active when bound to the carrier and/or spacer. In certain embodiments, an effective amount of the biologically active substance is delivered to the patient for more than one, two three days or a week or longer, following administration of a single dose of the pharmaceutical composition to the patient.

The carrier component of the CRDC can be a drug, a food substance, a polymer or an oligomer. Preferred drug carriers are those that have negligible therapeutic effect or detrimental side effects at a concentration in which it is released in the patient's body following administration of the conjugate. Among many others, mefloquine, chloroquine, hydrochloroquine, rifabutin, sirolimus, pimozide, tamoxifen and fluoxetine are drugs that are suitable for use as carriers. In certain embodiments, the carrier is a food substance selected from carotenoids and fatty acids. In other embodiments, the carrier is a bioresorbable oligomer or polymer or a non-bioresorbable oligomer or polymer.

The biologically active substance can be any class of substance, for example, selected from anesthetics, antidiabetic, bone metabolic modulators, cardiovascular agents, central nervous system depressants, gastrointestinal agents, antibiotics, antivirals, antiinfectives, antibacterials, antineoplastics, hormones, steroid agents, antiparkensonian, contraceptive, erectile dysfunction agents, analgesics, pain medications, anti-inflammatories, antilipidemic agents, diagnostic agents, antihistamines, peptide and proteins, urinary tract agents, psychotherapeutics, osteoporosis medications, immunomodulators and antiasthmatics.

In certain embodiments, the spacer component of the CRDC functions to increase or decrease the half life of the conjugate, as compared with an equivalent conjugate prepared without the spacer. The spacer can comprise one or more diols, diamines, diacids, aminoacids, aminoalcohols, hydroxyacids, dithiols, hydroxythiols, aminothiols, mercaptocarboxylates, dialkylsulfates, phosphate diesters, and phosphate triesters. In particular embodiments, the spacer comprises citric acid, tartaric acid succinic acid, glutaric acid, glycine, polyethylene glycol or modified polyethylene glycol.

In specific embodiments, the carrier is modified or unmodified mefloquine and the biologically active substance is zetia C-protected crestor, C-protected lipitor, rotigotine, meloxicam, piroxicam, N-protected carvediol, hydromorphone, N-protected albuterol, fluphenazine, detrol, atacand, trandolapril, perindopril, singulair, or zyrtec, wherein the conjugate optionally comprises the spacer. In other embodiments, the biologically active substance is hydromorphone, zetia, lipitor, crestor, atacand, ethinyl estradiol, 17 beta-estradiol, levonorgestrel, norgestimate, norethisterone and rotigotine; and the carrier is pimozide, tamoxifen, fluoxetine, linoleic acid, zeaxanthin, eicosapentaenoic acid, chloroquine, or hydroxychloroquine, wherein the conjugate optionally comprises the spacer. Exemplary embodiments include, but are not limited to: pimozide linked to hydromorphone, with an optional spacer; chloroquine linked to hydromorphone or rotigotine, with an optional spacer; fluoxetine linked to zetia, with an optional spacer; zeaxanthin linked to atacand, with an optional spacer; linoleic acid linked to zetia, crestor or lipitor, with an optional spacer; eicosopentaenoic acid, tamoxifen or chloroquine linked to ethinyl estradiol, with an optional spacer; and chloroquine linked to norethisterone, desogestrel or levonorgestrel, with an optional spacer.

Another aspect of the invention features a pharmaceutical composition comprising at least one controlled release drug conjugate (CRDC) comprising a biologically active substance linked to a carrier, and further comprising an optional spacer between the biologically active substance and the carrier, wherein the carrier has a half life of more than a day and the conjugate has a half life in a patient's body of more than one day, and optionally a pharmaceutically acceptable medium. The composition may be one in which the biologically active substance is released from the carrier in the patient's body. In certain embodiments, the pharmaceutical composition delivers an effective amount of the biologically active substance is delivered to the patient for more than one day, two days, three days, five days, or a week or more following administration of a single dose of the pharmaceutical composition to the patient. Typically the composition comprises a daily dosage of less than about 100 milligrams of the biologically active substance.

In some embodiments, the pharmaceutical composition also comprises an unconjugated form of the biologically active substance and, optionally, one or more excipients for facilitating controlled release of the unconjugated form of the biologically active substance for up to about one day following administration of a single dose of the pharmaceutical composition. In other embodiments, the pharmaceutical composition may also comprise one or more excipients for improving bioavailability, which can be selected from liposomes, micelles, nanoparticles and bioresorbable or non-resorbable polymers. In other embodiments, pharmaceutical composition also comprises one or more other active agents or controlled release drug conjugates of other active agents.

The pharmaceutical composition can be formulated for oral delivery or for parenteral delivery. Alternatively, it can be formulated for nasal, buccal, passive transdermal, iontophoretic transdermal, electrophoretic transdermal, microneedle transdermal, or skin ablation transdermal delivery.

Another aspect of the invention features method of extending delivery of a single dose of a drug to beyond one day from administration of the dose to a patient. The method comprises linking the drug to a carrier to form a drug-carrier conjugate, wherein the conjugate delivers the drug to the patient for more than one day from administration of a single dose of the conjugate. In certain embodiments, the drug is linked to the carrier through a spacer.

Another aspect of the invention features a dispenser for dispensing doses of a pharmaceutical composition comprising at least one controlled release drug conjugate comprising a biologically active substance linked to a carrier, and further comprising an optional spacer between the biologically active substance and the carrier, wherein the carrier has a half life of more than a day and the conjugate has a half life in a patient's body of more than one day and optionally a pharmaceutically acceptable medium. The dispenser comprises a plurality of compartments, each containing a dose of the pharmaceutical composition. The doses contained in the dispenser may be identical to one another, or they may be different from one another. In certain embodiments, the doses are serially available for use.

Other features and advantages of the invention will be understood by reference to the drawings, detailed description and examples that follow.

DETAILED DESCRIPTION OF ILLUSTRATIVE EMBODIMENTS

Figure 1A:
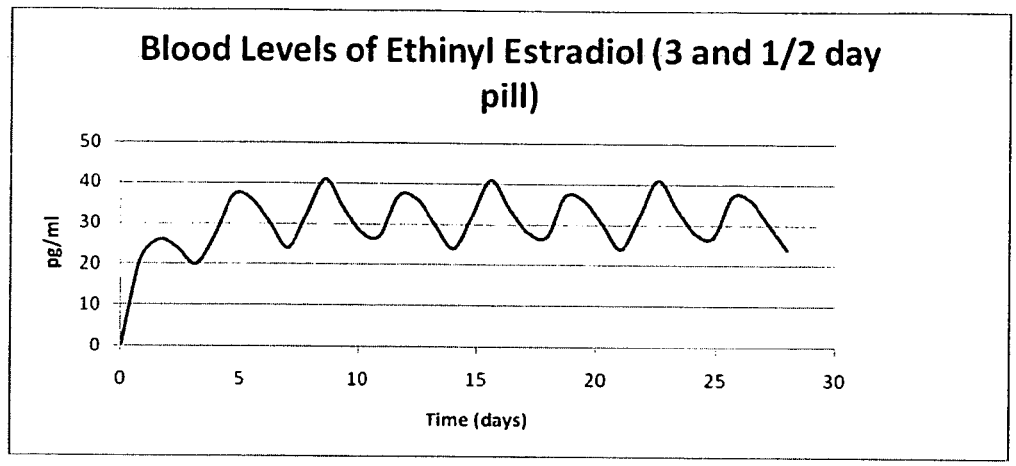
FIG. 1. Graphs showing predicted pharmacokinetic profile of orally delivered 3.5 day (FIG. 1A) or 7 day (FIG. 1B) ethinyl estradiol, calculated from hydrolysis rate of conjugate 1, mefloquine-succinate-ethinyl estradiol (Example 15).

Unless defined otherwise, all technical and scientific terms used herein generally have the same meaning as commonly understood by one of ordinary skill in the art to which this invention belongs. The nomenclature used herein and the laboratory procedures used in analytical chemistry and organic syntheses described below are those well known and commonly employed in the art. Standard techniques or modifications thereof, are used for chemical syntheses and chemical analyses.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations would be understood by the skilled artisan as appropriate to practice the present invention.

As used herein, the terms "drug," "biologically active substance," and the like, are used interchangeably herein to refer to a substance, or a composition containing one or more substances, having a biological activity or therapeutic effect in a human or animal.

Half life is defined as the time that it takes for 50% of the dosage absorbed into the body to be excreted from the body.

Multi-day delivery is defined as the delivery of an effective amount of a drug for more than one day, from the administration of a single dose of the drug. A "day" is 24 hours. The term "more than one day" refers to any amount of time over 24 hours, including hourly increments such as 25 hours, 26 hours and so forth, and further including smaller increments, such as fractions of hours, or minutes. In particular embodiments, multi-day delivery means delivery from, a single dose, of an effective amount of the drug for more than 1, 2, 3.5, 7, 15, 30, 60, 90, 180 or 360 days, or incremental periods within those time frames, preferably at a desired pharmacokinetic profile. It will be understood by the skilled artisan that, depending on the nature of the drug and initial dose, among other factors, an effective amount of a drug may exceed its half life. That is, even when more that 50% of a dosage has been excreted from the body, the amount remaining in the body may still be an effective amount for a period of time thereafter.

The terms "patient," "subject" or "individual" are used interchangeably herein and refer to a human or an animal that is the object of treatment, observation or experiment, inasmuch as the present invention is anticipated to have utility in human and veterinary medicine.

A single dose or single administration is defined as the dose of a drug that is delivered at approximately the same time and can be composed of one or more capsules or tablets, liquids, powders, dispersions, and the like.

As used herein, a "therapeutically effective amount" or an "effective amount" or an "efficacious amount" is the amount of a substance or composition sufficient to provide a beneficial effect to the individual to whom the substance or composition is administered.

It is understood that any and all whole or partial integers between any ranges set forth herein are included herein.

The various aspects of the invention described herein pertain to multi-day oral or parenteral delivery of biologically active substances to humans and other mammals, including for example the delivery of drugs, proteins, peptides, biologicals, vitamins, nutrients and biologically active substances for animal use, such as anthelmentics and estrus synchronization drugs. The compositions of the invention are referred to herein as controlled release drug conjugates, CRDCs. A CRDC comprises a carrier molecule with a half life that is longer than one day, either by itself or bound to a spacer as discussed below, or as part of the CRDC, a drug to be administered, which can be attached to the carrier molecule covalently, ionically, or by other means, and optionally a spacer molecule with appropriate chemical structure to be able to a) bond to the specific carrier molecule, b) bond to the specific drug to be delivered and optionally c) control the release of the drug molecule from the spacer after absorption of the CRDC into the body. Two general types of CRDCs are contemplated: (1) "direct" CRDCs, in which the drug is directly attached to the carrier molecule, and (2) "full" CRDCs, in which the drug is attached to the carrier molecule through a spacer molecule.

More specifically, aspects of the invention feature the release of one or more drug molecules at desired rates from CRDCs prepared by attaching the active drug to one or more carrier molecules, directly or by the use of one or more spacers. It should be understood that a CRDC may comprise (1) more than one drug or form of a drug, (2) more than one carrier or type of carrier, and/or (3) more than one spacer or type of spacer. For instance, two or more drugs, or forms of a drug, may be linked to a single carrier; a single drug may be linked to two or more carriers, and two or more drugs may be linked to two or more carriers. Likewise, the CRDC may comprise two or more spacers linking the drug(s) to the carrier(s).

The preparation of the CRDCs is discussed in detail below. Briefly, drug molecules suitable for use in the invention contain at least one functional group that can be used to attach them to a carrier or a spacer in a bioreversible manner. Some of the most common functional groups, that should be part of the carriers, spacers and drug molecules and which are amenable to the preparation of CRDCs include carboxylic, hydroxyl, amine, phosphate, phosphonate, thiol and carbonyl groups. CRDCs produced by modification of these groups include esters, carbonates, carbamates, amides, phosphates, oximes, thioethers, thioesters, imines and N-Mannich bases. All of these bonds can undergo an enzymatic and/or chemical transformation to release the drug from the CRDC and the spacer molecule from the carrier if desired.

The CRDCs are designed to release the drug(s) at predetermined rates and the drugs that are released from the conjugate to have the same structure and activity as the original drug. The carrier molecules should have acceptable side effect profiles with half lives in mammalian beings of at least one day, and more preferably of two or more days. Preferably, the carrier molecules are inert, at least at the daily dosages, released from the carrier/spacer/drug CRDCs, and have good bioavailabity. For example, for CRDCs that will be used in the oral delivery of a drug, the carrier molecule will preferably have good absorption through the mucosal tissue of the gastrointestinal tract, low gut wall metabolism and low hepatic metabolism.

Since in many cases the carrier molecules are modified using one or more spacers, the carrier/spacer molecules remaining after the drugs are released may be different from the original carrier molecules. It is essential that this new molecules have also acceptable side effect profiles and be safely eliminated from the body. Suitable carrier/spacer molecules should have acceptable side effect profile at the daily dosage delivered. In many cases, especially when the half life of the carrier is long, the drug can be released first, followed by the spacer. In this case both the carrier and the spacer should have acceptable side effect profiles.

In the simple case of carrier/drug (direct CRDCs), different carrier molecules, with different half lives can be selected, so the release profile of the drug meets the desired requirements. As it will be discussed in more detail below, the bond between the drug and the carrier in the case of the carrier/drug CRDCs or between the drug and the spacer of the carrier/spacer/drug-CRDCs should be hydrolytically, thermally, enzymatically, or by other means cleavable under physiologic conditions and the spacer should be preferably able to control this reaction.

Thus, typically, a CRDC consists of two or three classes of components: at least one carrier, at least one drug of interest and, optionally, at least one spacer. In cases where the drug can be attached directly to the carrier molecule, there may be no need for a spacer, but one may be included nonetheless to improve or modify delivery parameters. Preferred features of these three components are described below.

Carrier Molecules:

Preferred features of the carrier molecule include:

(1) It should have longer half life than the drug to be administered, at a minimum 24 hours and more preferably two days or more.

(2) It should have an acceptable side effect profile at the daily dose delivered.

(3) In general, it should not have any therapeutic or other biological effect at the dose delivered.

(4) It should be safely eliminated from the body after the drug is released from the conjugate.

(5) It should have at least one functional group that can be used to attach either the drug directly to it or indirectly through a spacer molecule. The bond between the carrier and the drug should be preferably cleavable under physiological conditions. The preferred bond is a covalent bond, but ionic or other bonds may be used.

Examples of such useful carrier molecules include drugs, food substances such as vitamins, nutritionals, sugars, peptides, proteins, oils, fatty acids, antioxidants, additives, as well as polymers and oligomers and other molecules designed specifically for that purpose.

Drugs can provide a preferred group of carriers since they have been thoroughly investigated and their pharmacodynamic and pharmacokinetic properties are well known. Certain drug molecules that are effective only at high doses and have no therapeutic value or unacceptable side effect profiles at lower doses are particularly suitable for use in the invention. The high doses mentioned above can be defined as being, for example, up to 2 or 3 times higher, on a molar basis, than those of the dose of the drug to be delivered. In other words, the molar ratio of the effective dosage (as a drug) of the carrier to the effective dosage of the drug to be delivered should be higher than about two or three. In preferred embodiments, it will be higher than about 2, 3, 4, 5, 6, 7, 8, 9, 10, 11, 12, 13, 14, 15, 16, 17, 18, 19 or 20 times higher. In some embodiments, the ratio will be even greater, e.g., more than about 50, 100, 150, 200, 250, 300, 350, 400, 450 or 500 times greater. In other embodiments, the ration may be yet higher, e.g., more than about 600, 700, 800, 900 or 1,000 times greater. It will be apparent to the person of skill in the art that if the carrier has a good side effect profile, then the above mentioned ratio can be closer to unity. The following drugs meet some of the above-listed criteria for carrier molecules, especially in respect to the half life requirements (half lives in parentheses). They are given here as examples, but should not be considered as limiting the invention to these specific drugs, as there are many other drugs that can be used in the invention: Nabumetone (23 hours), Nortriptyline (31 hours), Rifabutin (45 hours), Fluoxetine (53 hours), Donepezil (60 hours), Sirolimus (62 hours), Ivermectin (57 hours), Protriptyline (78 hours), Phenobarbital (99 hours), Pimozide (111 hours), Toremifene (148 hours), Infliximab (228 hours), Tamoxifen (4-11 days), Auranofin (17 to 25 days), Mefloquine (20+/−4 days), Gold sodium thiomalate (25 days), Avodart (35 days), Chloroquine (41 days), Hydroxychloroquine (51 days), (The Pharmacological Basis of Therapeutics, tenth ed. McGraw Hill, (2001) p. 1924 and Physicians Desk Reference 58$^{th}$ Ed. Thomson, 2004). Of these exemplary drugs, those with useful functional groups are preferred, although those with less useful structures may also be utilized, with appropriate chemical modification. As the skilled artisan will appreciate, any of the drugs mentioned above can be slightly modified to preserve the desired properties, but improve other properties such as increase or reduce their half life, reduce biological effect or improve side effect profiles.

Certain food substances can also be used as carriers. Food substances are defined herein as substances that are edible, absorb systemically and are used for sustenance or the well being of a mammal or a human being. Therefore, food substances comprise proteins, peptides, starches, sugars, oils, vitamins, antioxidants, preservatives, nutraceuticals, artificial substances such as sugar substitutes (aspartame, sucralose) and others. Many of the food substances mentioned above have relatively short half lives and they would be useful with the present invention in cases where the multi-day delivery is a few days, such as 2 or 3½ day delivery, of the chosen biologically active substance.

Other food substances have longer half lives, such as, for instance, carotenoids and fatty acids. For example the half lives of several carotenoids have been measured (J. of Nutrition 2001, 131, 2096). The half lives determined were: lutein 76 days, alpha carotene 45 days, beta cryptoxanthin 39 days, zeaxanthin 38 days, beta carotene 37 days and lycopene 26 days. The half lives of E and 5-Z lycopene have been found to be respectively 5 and 9 days (Eur. J. Nutr., 2004, vol. 43, #5, p 304).

The half lives of eicosapentaenoic acid (EPA) and docosahexaenoic acid (DHA) have also been measured. The half life of EPA in plasma phospholipids (PL) ranged from 1.63 to 2.31 days, whereas mean half life of EPA in cholesteryl esters (CE) was 3.27 days. Half lives for both EPA and DHA from triacylglycerols (TAG) followed a bi-exponential pattern with a short half life of less than a day followed by a half life of several days (Br. J. Nutr. 1999 December, 82 (6), 481). The half lives of sphingomyelins containing short or medium chain ($C_{16}$ to $C_{18}$) and long chain ($C_{20}$ to $C_{24}$) fatty acids have been studied. From the rate of decrease of the specific radioactivities of the different constituents of shorter chain fatty acid sphingomyelins, the half life was calculated to be 65 days for sphingosine, 41 days for fatty acids and 62 days for phosphates. For the long chain fatty acid sphingomyelins, the half life of sphingosine was about 465 days (J. Neurochemistry, Vol 27, issue 2, p 355, 1976). The half lives and mean transit times of alpha-linolenic acid and other n-3 fatty acids in plasma have also been determined (J. Lipid Res. 2001, 42 (8): 1257).

Polymers and oligomers can also be used as carriers for the delivery of biologically active substances both orally and parenterally. The advantages of some polymers and oligomers as carrier molecules are: (a) that they are known to last in the body for more than 24 hours, such as for example, the polyester based polylactic acid, polyglycolic acid, polycaprolactone, polydioxanone, trimethylene carbonate and polyhydroxyalkanoates such as polyhydroxybutyrate and polyhydroxyvalerate and their copolymers and terpolymers, (b) they are innocuous and without therapeutic effect, and (c) could have a plurality of active sites for attachment of a plurality of drug molecules or spacer/drug molecules, such as polyacrylic acid, polyacrylamides and polyvinyl alcohol. There are two categories of polymers and oligomers that can be considered: bioresorbable and non-bioresorbable. Bioresorbable polymers are those that when introduced into the human body degrade naturally due to hydrolysis, enzymatic degradation or other processes and are excreted from the body. In addition to the bioresorbable polymers mentioned above other bioresorbable polymer families include polyanhydrides, polyorthoesters, polyphosphazenes, polyamidoesters, tyrosine based polymers and copolymers and cyanoacrylate copolymers among others. A major family of natural water soluble polymers that includes many bioresorbable polymers is the polysaccharide family of polymers. Polysaccharides include galactans such as agars, agaroses and carageenans; galactomannans such as locust bean gum and guar; glucans such a cellulose and derivatives (carboxy methyl cellulose), starches and derivatives, dextrans, pullulan, 1,3 glucans, chitin/chitosan and xanthan; polyuronic acids such as alginates and pectins; heteropolysaccharides such as gellan, okra gum and karaya gum; animal polysaccharides such as chondroitin sulfates, hyaluronic acid and dermatan. The above mentioned polymers as well as most other bioresorbable polymers can be modified to improve their properties as carrier molecules, and still remain bioresorbable. For example chitosan can be modified by carboxymethylation to give N,O-Carboxymethylchitosan which provides for additional reactive sites and still preserve a time to bioresorption of more than one day. Similarly, N,O-Carboxymethylchitosan can be further crosslinked with for example a dialdehyde, such as gluteraldehyde or glyoxal, or through a carbodiamide reaction to form crosslinked polymers. These modified polymers which are still bioresorbable have degradation rates in the human body of several weeks depending on the degree of crosslinking. Therefore, the present invention contemplates the use of bioresorbable polymers as well as well as modified bioresorbable polymers as carriers.

Synthetic non-bioresorbable polymers, in addition to some of the polysaccharides mentioned above, include polyvinyl alcohols, polyacrylamides, polyacrylic acids, polyurethanes, polyvinyl pyrrolidones, polyamides, oxirane polymers, polyethylene oxides, polyethylene glycols, maleic anhydride based copolymers and many other polymer families, well known to the person of skill in the art. Particularly suitable are the polyvinyl alcohols, polyacrylamides and polyacrylic acids, due to the presence of a plurality of hydroxy, amino and carboxylic acid groups on their polymer backbones, respectively. For optimum utility, the non-bioresorbable polymers will be modified so as to allow their excretion from the body. Substances including non-bioresorbable polymers of less than 50,000 daltons in molecular weight can be excreted from the body, while molecules with higher molecular weight cannot be excreted due to renal filtration. As an example oligomers of non-bioresorbable polymers can be prepared with molecular weights of less than 50,000 daltons and then connected together by cleavable or biodegradable linkages or crosslinked together by cleavable or biodegradable crosslinkers. When the cleavable or biodegradable linkers or crosslinkers are broken down, by hydrolysis, enzymatic degradation or other means, the oligomers are released, and can then be removed from the body, since their molecular weight is less than 50,000 daltons. It is important that the rate of cleavage of the linkages or crosslinkers connecting together the oligomers is slower than the rate of cleavage of the linkages between the drug to be released and the polymer, in the case of direct conjugates, or the rate of cleavage of the drug to be released from the spacer, in the case of full conjugates. It is most favorable for the fastest rate of release to be between the spacer and the drug to be released, so pure drug becomes available in the body. This will become more obvious in further discussions of various aspects of the invention. It is therefore another embodiment of the present invention, to utilize as carriers, non-resorbable polymers and other materials which comprise oligomers or other molecules of less than 50,000 daltons in molecular weight and which may be linked together with cleavable bonds.

In the oral delivery of conjugates based on polymeric carriers, it will be necessary to have appropriate absorption of the conjugates into the systemic circulation. A large pool of information and technologies has been assembled for the oral delivery of large molecules to the body and an industry has sprung to address the oral delivery of macromolecules including proteins. Some of these technologies include the use of intestinal permeation enhancers (J. Pharm. Sci; Vol 89, No 4, April 2000), epithelial tight junction openers (J. Control. Release 64, 15, 2000), liposome encapsulation (Pharm. Res. 13, 1378, 1996), micelle encapsulation and nanoparticle formation. These methods, among many others can be employed to deliver the polymeric conjugates of the present invention to the systemic circulation.

New carrier molecules can also be engineered that would have the appropriate half lives and have no therapeutic or side effects. This for example can be accomplished by modifying the above mentioned carrier molecules to preserve the half life. Totally new molecules can also be engineered, since the main property that one needs to obtain is that of half life. Half life ($t_{1/2}$) is the time it takes for the plasma concentration or the amount of the drug in the body to be reduced by 50%. Half life is really a derived parameter based on the two most important properties of pharmacokinetics, volume of distribution (V) and clearance (CL). Clearance is the measure of the body's ability to eliminate the substance from the body and volume of distribution relates the amount of the substance in the body to that in the blood or plasma (Pharmacokinetics, M. Gibaldi and D. Perrier, ed., Marcell Decker, Inc (1982) and The Pharmacological Basis of Therapeutics, Gilman et al, eds., p 3. (1990)). Thus the relationship between clinically relevant half life, volume of distribution and clearance can be given by the equation:

$$t_{1/2} = 0.693 \cdot V/CL$$

In general, when the volume of distribution increases the half life increases and when the clearance increases the half life decreases. These two pharmacokinetic parameters are well understood and can be measured for any substance, thus allowing for the engineering of new carrier molecules.

Polymeric carriers can also be tailor-made by synthesizing new polymers or through modification of existing polymers to optimize their properties as carrier molecules.

Drug Molecules:

The preferred features of drugs to be delivered using the present invention are:

(1) Drugs should have functional groups, preferably hydroxyl groups, amino or carboxylic acid groups that can be reversibly attached to the carrier, either directly or through a spacer. Other functional groups, such as those mentioned above can also be used.

(2) The drug preferably should be effective at low doses. Specifically, the therapeutic dosage requirements for the drug molecules should be considerably lower, on a molar basis, than the therapeutic dosage of the carrier molecules so that the carrier molecules released do not produce unacceptable side effect profiles, as described above.

In general, most drugs can be used with the present invention, depending on the choice of carrier molecule(s) and/or spacer(s). Drugs that have the functionalities mentioned above and are therapeutically effective at lower dosages would be preferred candidates. Without limiting the invention, some examples of such preferred drugs would be, cholesterol lowering drugs (Zetia, Crestor, Lipitor), schizophrenia drugs (Xyprexa, Risperdal, Abilify), seizures/parkinson's drugs (Rotigotine, Selegiline), depression drug (Lexapro), benign prostate hypertrophy drugs (Flomax, Avodart, Proscar, Hytrin), ADHD drugs (Adderal, Methylphenidate), Alzheimers drugs (Exelon, Aricept), arthritis drugs (Meloxicam, Piroxicam), diabetes drugs (Amaryl, Avantia), gastrointestinal drugs (Nexium, Prevacid), hypertension drugs (Atacand-ARB, Coreg-Alpha/Beta Blocker, Plendil-Calcium Channel Blocker, Isradipine-Calcium Channel Blocker, Polythiazide—Diuretic, Indapamide—Diuretic, Trandolapril-Ace I, Perindopril-Ace I), pain drugs (Hydromorphone, Hydrocodone), asthma drugs (Albuterol, Singulair, Zyrtec), anxiolytic/antipsycotic drugs (Haloperidol, Fluphenazine, Ativan, Xanax), antiemetic drugs (Zofran, Kytril, Tetrahydrocannabinols), drugs for overactive bladder (Detrol, Oxybutynin), erectile dysfunction drugs (Viagra), hormone drugs (estradiol, norgestimate, ethinyl estradiol, levonorgestrel, progesterone, testosterone), and cancer drugs (erlotinib, tretinoin, levothyroxine), to name a few. As mentioned above, some of these drugs may require modification in order to be converted to CRDCs due to absent or difficult functionalities. However, there are many other drugs that have not been mentioned above that could be included in the above mentioned preferred list. Peptides and proteins would be other biologically active substances of interest, since they always have appropriate functionality for conjugation, have very short half lives and they are therapeutically effective at extremely low doses.

Spacer Molecules:

The type of spacer used depends on the functional groups present and available on the specific carrier and drug molecules to be used. The most preferred functional groups that can be present in the carrier molecules are amino, carboxylic, and hydroxyl. The other functional groups mentioned hereinabove would also be appropriate.

Preferred spacer molecules have one or more of the following features:

(1) The molecules should be safe and non toxic.

(2) They should have at least two functional groups, one for attaching to the carrier and the others for attachment to the drug or drugs.

(3) It should be possible to tune in the release rate of the drug from the CRDCs by varying the structure of the spacer or the type of spacer, as will be shown in more detail below.

(4) The spacer used will need to have the appropriate chemical structure, so as to accommodate the functional groups on the carrier molecules, the functional groups on the drugs to be released and the desired release rate of the drugs. Most preferably the bond between the spacer and the carrier molecule should be stronger than the one between the spacer and the biologically active substance.

The spacer molecules are an important component of the invention. There are a great number of spacers that could be used, including diols, diamines, diacids, aminoacids, aminoalcohols, hydroxyacids, dithiols, hydroxythiols, aminothiols, mercaptocarboxylates, dialkylsulfates, phosphate diesters, and phosphate triesters, to name a few, and in particular, spacers such as citric acid, tartaric acid succinic acid, glutaric acid, glycine, PEG and modified PEGs with the one side amine terminated and the other side hydroxyl terminated and many others as it will become obvious from the discussion below. Shown below are five different schemes for the use of spacers, depending on the functional groups on the carrier or drug molecules. It will be understood by the skilled artisan that many other schemes can be developed to accommodate various other circumstances. These schemes are examples of the use of the spacers with different carrier and drug molecules and they are not to be used to limit the breadth of the invention, since many other spacers, carrier molecules and reactions can be utilized in accordance with the principles described herein.

Scheme 1.

Spacers for Amino Groups in the Carrier Molecule.

Shown below is a reaction scheme to attach a small spacer to a carrier molecule that contains a functional amino group. A free carboxylic acid group is present in the non-reacted side of the spacer for attachment of the drug. The R group at the alpha carbon can be varied depending on the rate of release required. For example, an electron withdrawing R group increases the rate of release, while a bulky R group can decrease the rate of release due to steric hindrance. When longer spacers are used, the R group can be allowed to randomly attach to the backbone of the spacer, which can provide different but reproducible release rates of the drug. The R group can be a biodegradable group such as an ester group, which will protect the bond between the drug and the spacer, but it will be cleaved during the passage of the conjugate through the intestinal wall and the liver. The starting materials are commercially available and the reactions are well known. The spacer shown in the scheme below is based on melonic acid; however, many other di-acid based spacers and other spacers can also be used, such as for example, succinate, N-acetylglutamate, glutarate and N-acetylaspartate, or any of the other spacers listed hereinabove. Therefore, the release of the active drug from the CRDC can be controlled by the use of different spacers as well as from the type of group attached in the R position as explained above. It should be kept in mind that the longer the spacer, the longer the distance between the carrier and biologically active substance. This would allow for the carrier molecule to better preserve its original properties, such as that of the long half life.

Scheme 1. Spacer for attachment to an amino group containing carrier.
The R group on the alpha carbon can be varied to obtain desired rate of release
of the drug attached to the COOH group as ester. R = H, Me, iPr, iso-butyl, amyl, and the like.

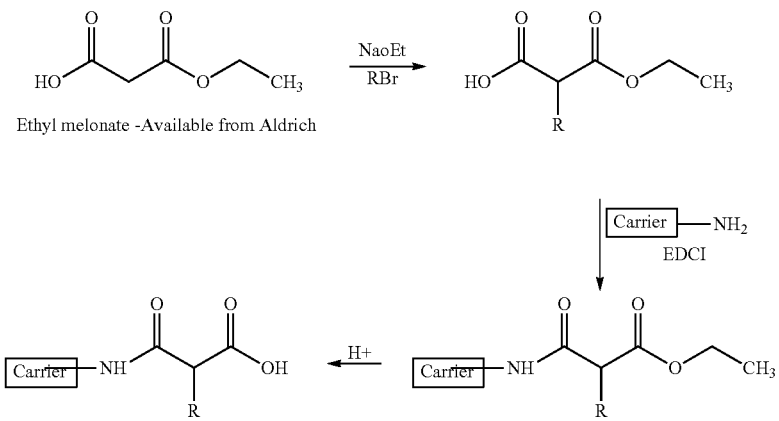

Scheme 2.

Spacers for Carboxylic Acid Groups in the Carrier Molecule.

The spacer can be appropriately modified to accommodate a carboxylic acid group in the carrier molecule. The COOH group on the spacer is converted to an amino group using ethylene diamine. The rest of the reactions are similar to those in Scheme 1. All reactions in Scheme 2 are well known to the person of skill in the art.

Scheme 2. Then COOH on the spacer is converted to an amine which
then can react with a carboxylic acid group on the carrier molecule

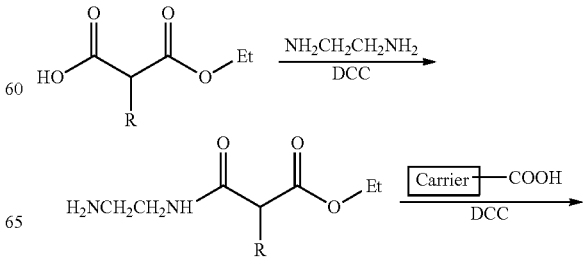

-continued

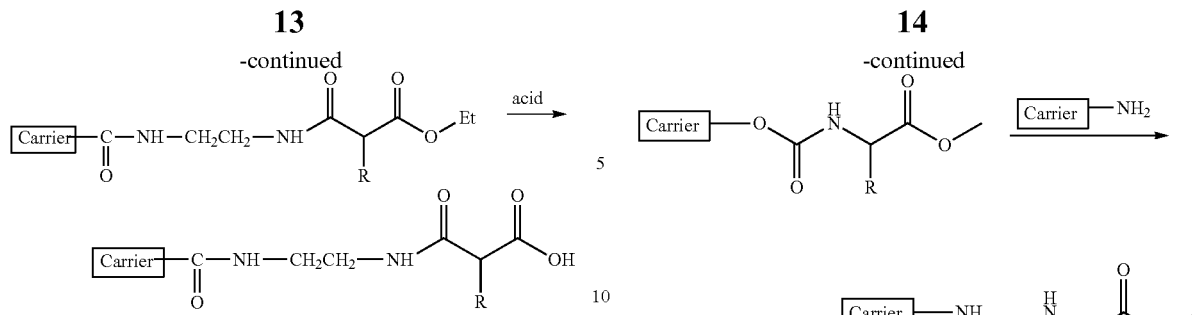

Scheme 3.

Spacers for Hydroxyl and Amino Groups in the Carrier Molecule.

The spacer containing amino group in Scheme 2 can be reacted with phosgene to convert it into an isocyanate group. The isocyanate group forms a urethane linkage with the hydroxy group on the carrier molecule as shown below. The isocyanate group can also be reacted with the amino group on the carrier (not shown) to form a urea bond. These reactions are well known to the skilled artisan.

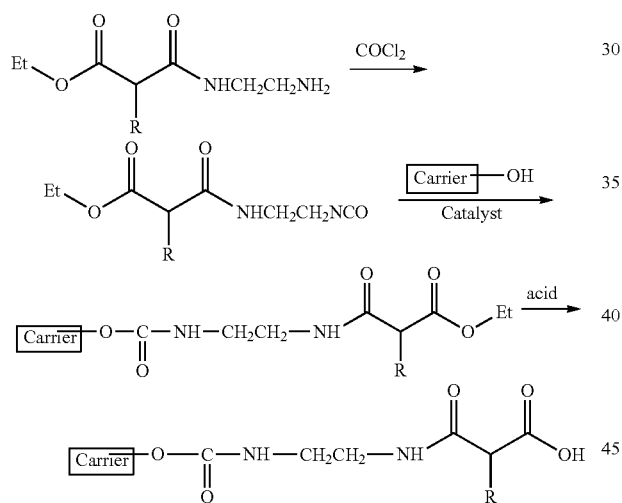

Scheme 3a. The amino group on the spacer is converted to an isocyanate group with phosgene. The isocyanate then can react with the hydroxyl group of the carrier molecule Another useful family of spacers is a series of compounds containing both isocyanato and ester groups. Examples of such compounds are methyl 2-isocyanatobutyrate, ethyl 3-isocyanatopropionate, ethyl 2-isocyanatoacetate, ethyl 2-isocyanatoformate etc which are commercially available. These can be used to react with carrier molecules containing either hydroxyl or amino groups, as shown in Scheme 3b.

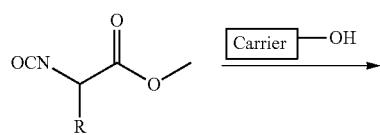

Scheme 3b. Commercially available spacers for modification of carriers with hydroxy and amino groups. R can be varied to control the release rates of drugs to be attached

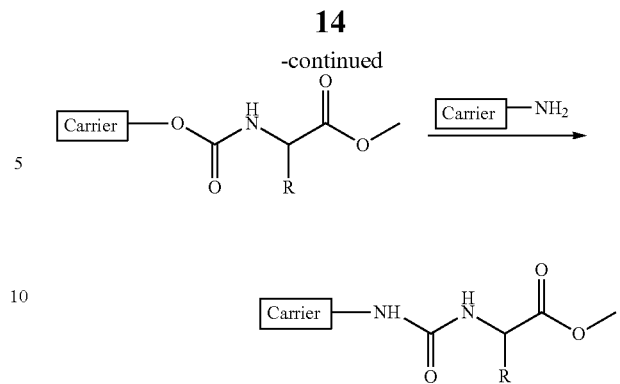

Scheme 4.

Conversion of the Carrier/Spacer/Ester to Carrier/Spacer/OH.

In all of the above examples, after the reaction of the spacer onto the carrier molecule, the functional group remaining on the carrier/spacer combination is a carboxylic acid group. This is particularly suitable for reaction with drugs containing hydroxy groups. Many drugs, however, contain functional groups such as carboxylic acid groups, amino groups and even carbonyl groups (aldehyde and keto groups). In this case the spacer has to be suitably modified. This can be converted to a hydroxyl group by reduction with lithium aluminum hydride (LAH) as shown below.

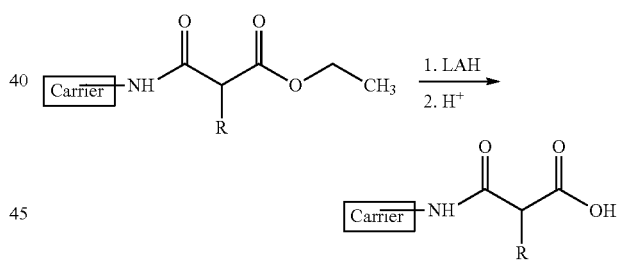

Scheme 4. Reduction of the ester group to the corresponding hydroxy group with lithium aluminum hydride (LAH). This reduction can be carried out with all the molecules shown in the Schemes 1, 2 and 3.

Scheme 5.

Spacers for the Attachment of Drugs with Amino Groups.

Amino groups can be converted to amides, carbamates, N-Mannich bases, oximes, imines, urethanes, or hydrazones. Amides and urethanes are not easily cleaved hydrolytically. However, under certain circumstances the urethanes can be made to cleave hydrolytically. Two such cases are shown below.

a) The spacer in this case is derived from 4-hydroxy benzyl alcohol. The phenolic group is attached to the carrier via an ester linkage and the alcohol group is activated using p-nitrophenyl chloroformate. The resulting compound is reacted with a drug containing an amino group as shown below.

Scheme 5a. Spacer for the attachment of drugs containing amino groups to a drug carrier.
In this case the urethane bond cleaves under physiological condition by a mechanism shown in Scheme 5b.

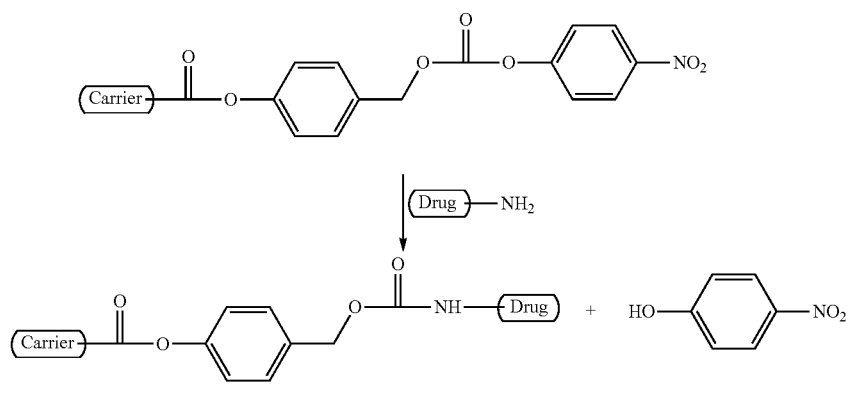

The CRDC shown above is hydrolyzed under physiological pH by a mechanism shown in Scheme 5b. The carrier molecule and the drug are released along with other innocuous byproducts (Advanced Drug Delivery Reviews, 55, (2003), 217-250).

Scheme 5b. Mechanism of release of the drug and the carrier from the CRDC shown in Scheme 5a

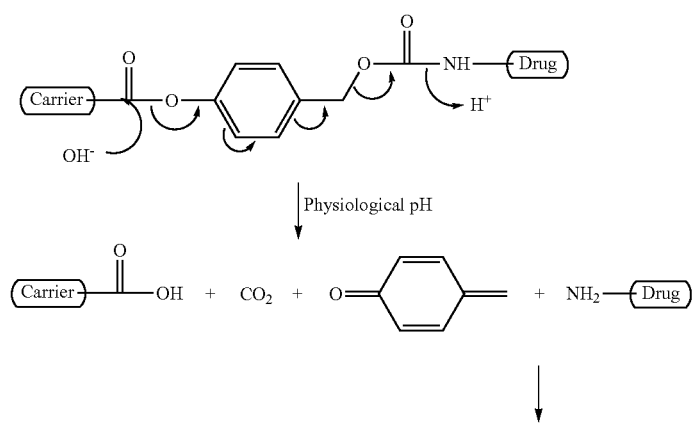

b) The amine containing drugs can also be attached using a hydrazone linkage. For this the carrier or the spacer should contain an aldehyde or a keto group Scheme 5c. Hydrazone derivative of drugs with amno group

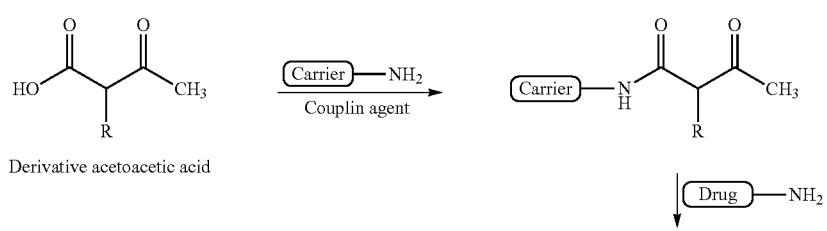

Derivative acetoacetic acid

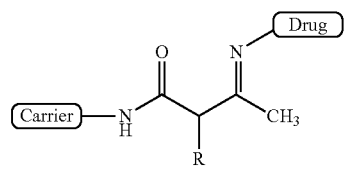

Drug Release from Conjugates (CRDCs)—Effect of Different Moieties on the Hydroxide ion Catalyzed Hydrolysis of Esters.

The rate of release of the drug by ester hydrolysis depends on the substituent on the alcohol and the acid portion of the ester. In general, if the alcohol is sterically hindered, the rate of hydrolysis decreases. Electron withdrawing groups on the alcohol, especially near the α-carbon, increase the hydrolysis rate. Phenolic esters hydrolyze faster than the alkyl esters. The following Table 1 shows how the rate of hydrolysis is affected by the substituents on the alcohol portion of the ester.

Substituents on the acid moiety of the ester also show marked influence on the rate of hydrolysis. In general, the substituent effects are similar as with alcohols. Examples of this are shown in Table 2. The esters in Tables 1 and 2 are chosen from several hundred described in the literature (Comprehensive Chemicals Kinetics, volume 10, Ester Formation and Hydrolysis and Related Reactions, Bamford C. H., and Tipper C. F. H., eds, Elsevier Publishing Company, Amsterdam, 1972).

TABLE 1

Effect of the alcohol moiety on the hydroxide ion catalyzed hydrolysis of esters

| Ester | Solvent | Temperature | $k_{OH}$ L.mol$^{-1}$.sec$^{-1}$ |
|---|---|---|---|
| $CH_3COOCH_3$ | 70% acetone | 24.7 | 0.108 |
| $CH_3COOC_2H_5$ | 70% acetone | 24.7 | 0.047 |
| $CH_3COO(CH_2)_2CH_3$ | 70% acetone | 24.7 | 0.027 |
| $CH_3COOCH(CH_3)_2$ | 70% acetone | 24.7 | 0.007 |
| $CH_3COOC(CH_3)_3$ | 70% acetone | 24.7 | 0.00027 |
| $CH_3COOCH_2C_6H_4NO_2$ (para) | 60% acetone | 25 | 0.269 |
| $CH_3COOC_6H_5$ | 60% acetone | 25 | 0.537 |
| $CH_3COOC_6H_4NO_2$ (para) | 60% acetone | 1 | 2.2 |
| $CH_3COOC_6H_4CH_3$ (meta) | 60% acetone | 1 | 0.09 |

TABLE 2

Effect of the acid moiety on the hydroxide ion catalyzed hydrolysis of esters

| Ester | Solvent | Temperature | $k_{OH}$ L·mol$^{-1}$·sec$^{-1}$ |
|---|---|---|---|
| $CH_3COOC_2H_5$ | 70% acetone | 24.7 | 0.047 |
| $nC_3H_7COOC_2H_5$ | 70% acetone | 24.7 | 0.088 |
| $(CH_3)_3CCOOC_2H_5$ | 70% acetone | 24.7 | 0.00022 |
| $(C_2H_5)_2CHCOOC_2H_5$ | 70% acetone | 24.7 | 0.000083 |
| $ClCH_2COOC_2H_5$ | Water, µ = 0.2 | 24.7 | 33.2 |
| $CH_3SCH_2COOC_2H_5$ | water | 24.7 | 0.92 |
| $CH_3SOCH_2COOC_2H_5$ | water | 24.7 | 4.20 |
| $(CH_3)_3N^+CH_2COOC_2H_5$ | water | 24.7 | 98.0 |
| $H_3N^+CH_2COOC_2H_5$ | water | 24.7 | 60.5 |

These effects can be easily understood from the mechanism of the ester hydrolysis shown below. Bulkiness of R, R' and R" would make the attack by the hydroxide ion more difficult and hence the rate would decrease. Electron withdrawing groups on R' would stabilize the negative charge on the leaving group (R'O⁻) and make the alkoxide better leaving group. Electron withdrawing groups on R or R" would increase the positive charge at the carbonyl carbon and the attack by hydroxide ion becomes more facile.

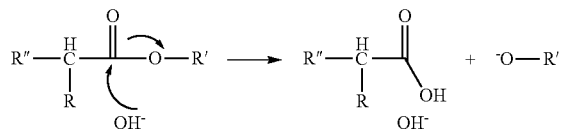

It is apparent from the mechanism shown above that, although the drug release is controlled mainly by the functionality of R in the spacer molecule, the structure of the carrier molecule and the drug also contribute to the kinetics of drug release. Therefore, although the release kinetics of the drug and the half lives of the carrier are presented independently, the interactions between all of the components of the CRDC, the carrier, spacer and drug molecules are important in determining these properties of the CRDC. The release kinetics involved in the splitting of the esters, can be chemically or enzymatically controlled, especially by the esterase enzymes such as human carboxylesterases 1 and 2 which are involved in drug metabolism (reviewed in Drug Metab. Pharmacokinet. 21 (3): 173 (2006)).

The invention encompasses pharmaceutical compositions comprising CRDCs. Such pharmaceutical compositions may include a one or more CRDCs, in a form suitable for administration to a subject, or the pharmaceutical composition may comprise one or more CRDCs and one or more pharmaceutically acceptable excipients, one or more additional ingredients, or some combination of these in a pharmaceutically acceptable medium. The active ingredient may be present in the pharmaceutical composition in the form of a physiologically acceptable ester or salt, such as in combination with a physiologically acceptable cation or anion, as is well known in the art.

As used herein, the term "pharmaceutically acceptable medium" means a chemical composition (solid, liquid or gas, or any combination) with which a CRDC may be combined and which, following the combination, can be used to administer the CRDC to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The CRDCs are preferably formulated in dosage form for ease of administration and uniformity. "Dosage form" or simply "dosage" as used herein refers to a physically discrete unit of a CRDC, or pharmaceutical composition comprising CRDCs and, optionally, other active agents, appropriate for the patient to be treated. Each dosage should contain the quantity of active material calculated to produce the desired therapeutic effect either as such, or in association with the selected pharmaceutical medium and/or the supplemental active agent(s), if any.

Though the CRDCs are particularly suitable for oral or parenteral administration, they can be administered orally, rectally, parenterally, such as by intramuscular injection, subcutaneous injection, intravenous infusion, implantation or the like, intracisternally, intravaginally, intraperitoneally, locally, such as by powders, ointments, or drops, or the like, or by inhalation, such as by aerosol or the like, or transdermally, by a passive or active transdermal route, e.g., iontophoretic transdermal, electrophoretic transdermal, microneedle transdermal, or skin ablation transdermal, taking into account the nature and severity of the condition being treated.

For instance, for oral administration in the form of a tablet or capsule, the CRDC can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like. For liquid forms the CRDC can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous, intraperitoneal, intramuscular or subcutaneous administration is desired.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Depending on the route of administration, the compounds of the invention may be administered at dosage levels of about 0.005 to about 100 milligrams per day, less frequently than one time per day, preferably once every other day, or every three, four, five or six days, or once weekly, once every other week or once monthly. Intervals between administrations could be even greater, depending on the half life of the CRDC in the body, the nature of the condition being treated, the dosage required, and similar considerations familiar to the medical professional.

Another aspect of the invention features a dispenser for the delivery of the pills, capsules and other dosage forms of the invention. For example, a dial pack similar to those used for dispensing ovulation control pills is appropriate for the delivery of the dosage forms of the invention. In certain embodiments, the dispenser comprises a section for the positioning of several pills or capsules. Each of the pills or capsules can be of different drug strength and of different drug release rate, so as to optimize the rapid attainment of the proper drug release profile that is desired. Therefore, in some embodiments, an integral part of the dispenser's properties is to provide a safe method of delivering the pills or capsules, serially. In these embodiments, the dispenser should allow only for the removal of the first pill or capsule. When the first pill is removed, the dispenser can then dial the release of the second pill. The process can be repeated until all pills or capsules are removed. This feature is referred to herein as having the dosages "serially available." Such a dispenser for the delivery of dosage forms of the invention advantageously allows for the serial removal of the dosage forms, to provide safety and delivery of each dosage at the appropriate and predetermined time. There are many different, basic and well known mechanical and electromechanical ways to prepare the above mentioned dispensers.

The following examples are provided to describe the invention in greater detail. They are intended to illustrate, not to limit, the invention. Using the strategies described above, here below are shown examples using specific carrier molecules and spacers to prepare CRDCs. Selection of the carrier and spacer depends on the rate of release of the drug desired and the type of functional group on the drug to be released. As described earlier the R group on the spacer is chosen with this in mind. For instance, when a faster release is preferred, the R group may be an electron withdrawing group, whereas alkyl groups generally slow down the release. When the alkyl groups are bulky the release rate may be further retarded due to steric hindrance. It is another embodiment of my invention to prepare different carrier/spacer molecules with different groups in the R position, as mentioned above, and to react the carrier/spacers with the specific drug. The different carrier/spacer/drug conjugates thus produced can then be mixed at the appropriate proportions in the dosage form as to achieve the desired release rate profile. Typical examples of CRDC preparations are given in hypothetical Examples 1-13. Each hypothetical example employs standard chemistry well known to the skilled artisan. Examples 14-17 describe actual syntheses and experimental results, while Examples 18 and 19 describe calculations derived from actual experimental results.

Example 1

Mefloquine as Carrier for Drugs with Hydroxyl Groups

Mefloquine which has a half life of 20+/−4 days has a secondary amino group and a primary hydroxyl group. This can be modified so that drugs containing hydroxyl groups and phenolic groups can be attached to it via an ester linkage in accordance with the reaction scheme shown below. The hydrolytic cleavage rate of the esters can be controlled by varying the R group.

Exemplary Reaction Scheme 1. Modification of Mefloquine and attachment of drugs with OH groups to the modified molecule for sustained release of drugs

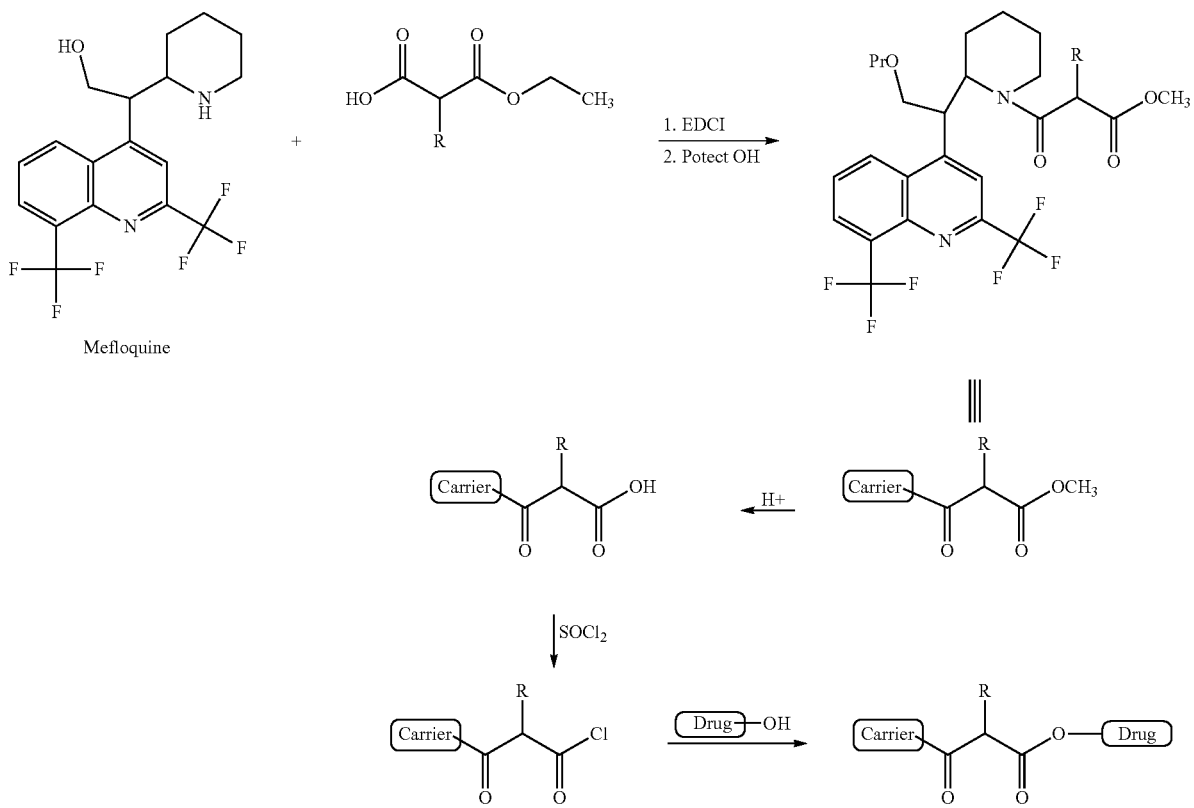

Some examples of drugs that can be modified in this fashion are the following: Zetia, C-protected Crestor, C-protected Lipitor, Rotigotine, Meloxicam, Piroxicam, N-protected Carvediol, Hydromorphone, N-protected Albuterol (multiple OH groups), Fluphenazine and Detrol.

A number of other drug molecules can be used as carrier molecules, such as chloroquine ($t_{1/2}$=41 days), structure shown below), fluoxetine (($t_{1/2}$=53 h), protriptyline ($t_{1/2}$=76 h) which contain a secondary amine in their structure and they can be modified using similar procedures. In this case, however, there is no hydroxyl group present and hence it involves one less reaction step.

Example 2

Mefloquine as Carrier for Drugs with Carboxylic Acid Groups

Mefloquine can also be used as a carrier for drugs containing carboxylic acid groups. For this purpose the primary hydroxyl group is utilized as shown in the reaction scheme below. It should be noted, however, that since the drug is attached directly to the mefloquine carrier without the use of a spacer, the release rate can not be manipulated by way of the spacer in this example.

Exemplary Reaction Scheme 2. Modification of Mefloquine to attach drugs containing carboxylic acid group

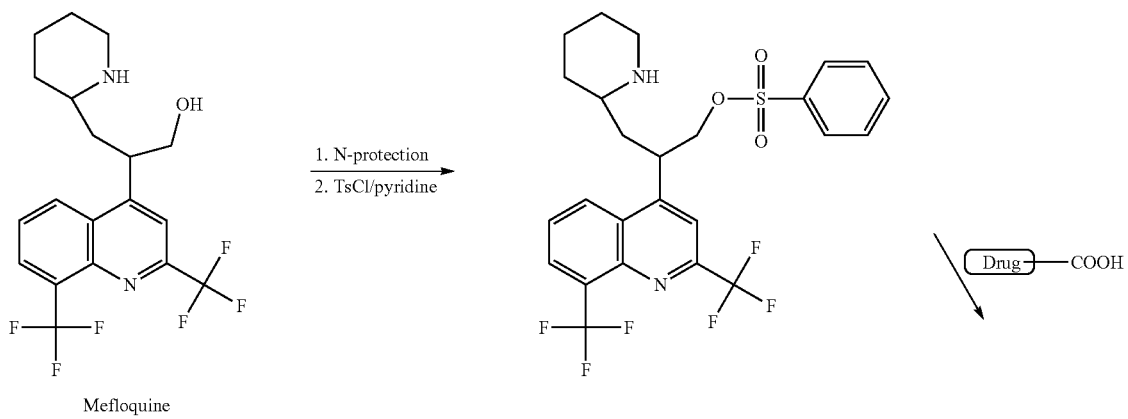

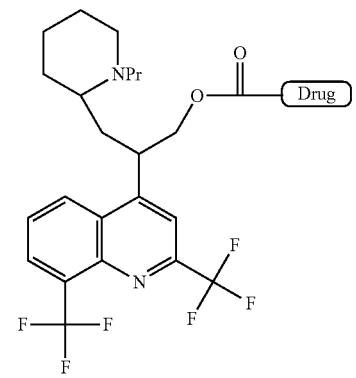

For example, drugs such as Atacand, Trandolapril, Perindopril, Singulair, and Zyrtec that have free carboxylic acid groups can be used in accordance with the above reaction scheme.

Example 3

Chloroquine as Carrier for Drugs with Carboxylic Acid Groups

For attachment of drugs containing carboxylic acid groups, a different strategy is employed, using any of the carrier molecules that contain an amino group. The scheme below

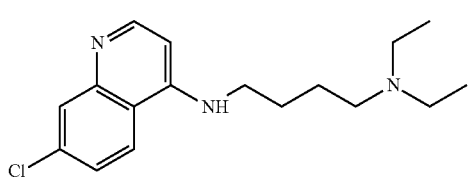

Structure of chloroquine shows the modification of chloroquine. The secondary amino group of chloroquine is coupled with suitably substituted melonic acid monoethyl ester followed by reduction with lithium aluminum hydride to the corresponding alcohol. The hydroxy group is activated with p-toluene sulfonyl chloride followed by reaction with the drug.

Exemplary Reaction Scheme 3. Modification of drugs containing carboxylic acid groups for sustained release

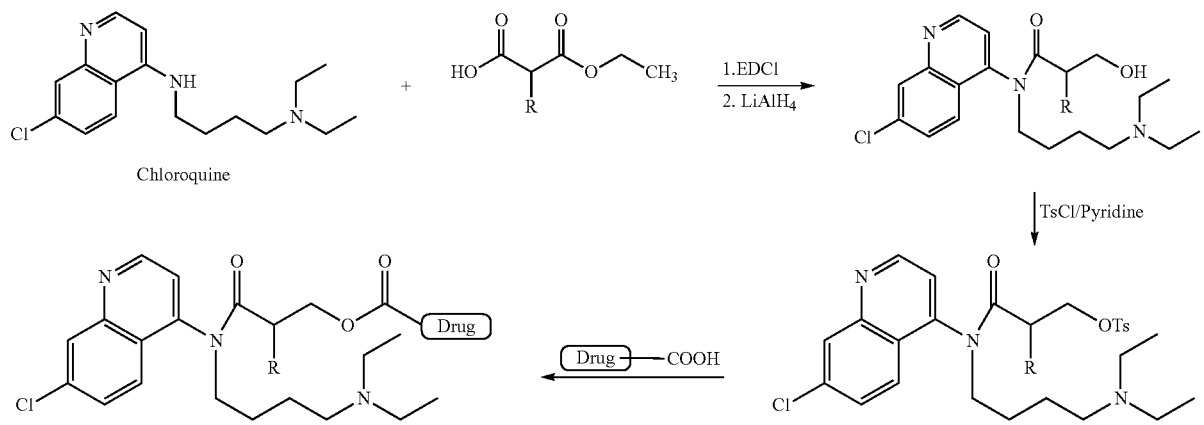

These modifications can also be carried out with other carrier molecules as mentioned above, that contain amino groups.

Example 4

Multiple Drug Molecules on a Carrier

When a carrier molecule has more than one functional group they can be utilized to attach multiple drug molecules of the same drug or two or more molecules of different drugs. Rifabutin ($t_{1/2}$=45 h) is a typical example. It has two secondary hydroxy groups and a phenolic group that can be utilized for the attachment of two or three drug molecules directly to Rifabutin (Exemplary Reaction Scheme 4a) or via a spacer (Exemplary Reaction Scheme 4b).

Exemplary Reaction Scheme 4a. Attachment of two drug molecules directly to Rifabutin for controlled release

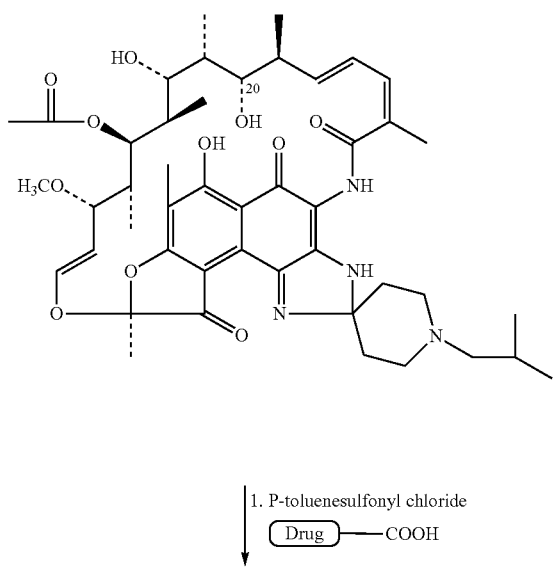

-continued

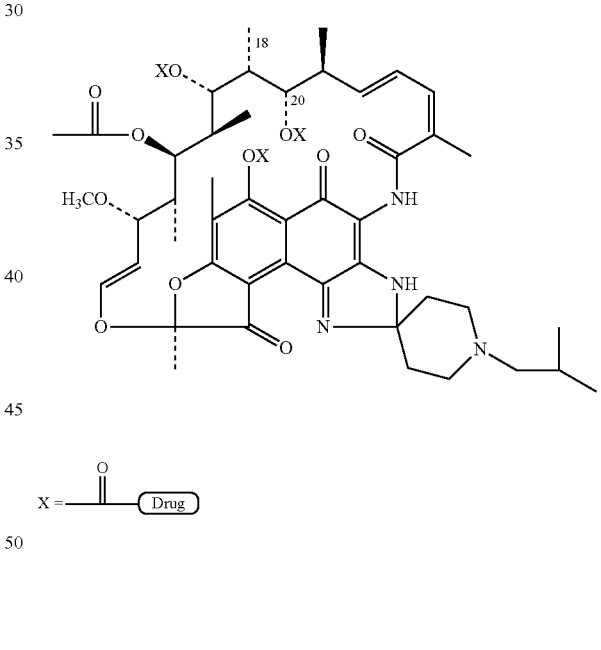

When the drug has a hydroxy group, a spacer can be used as shown in Exemplary Reaction Scheme 4b. Some such spacers are available commercially (e.g. methyl 2-isocyanatobutyrate, ethyl 3-isocyanatopropionate, ethyl 2-isocyanatoacetate, ethyl 2-isocyanatoformate). Others can be easily prepared from ethyl 2-isocyanatoacetate.

Sirolimus ($t_{1/2}$=62 h) also contains 2 secondary hydroxy groups and it can be modified using the same strategy. Two drug molecules can be attached to this carrier as well.

Exemplary Reaction Scheme 4b. Modification of rifabutin with a spacer to use it as carrier for drugs with hydroxy groups. The R group in the spacer determines the rate of drug release

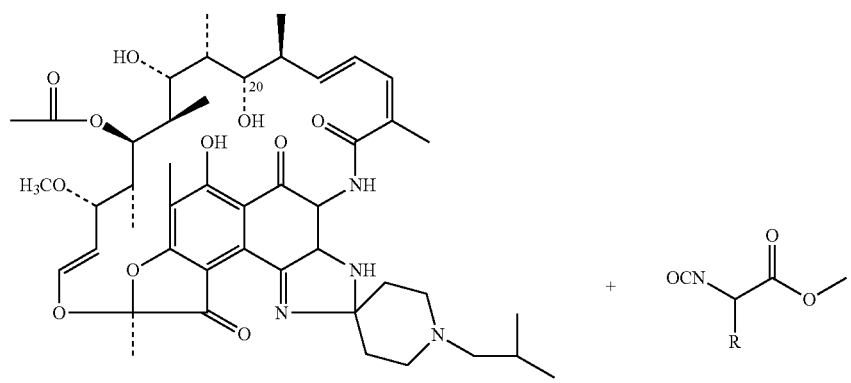

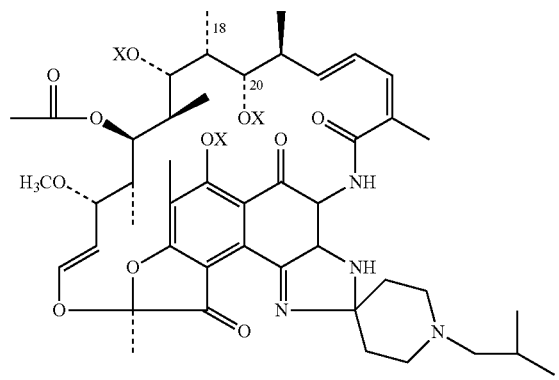

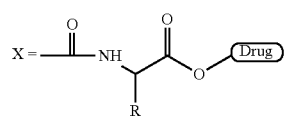

Example 5

Modification of Pimozide (Half Life, 111 Hours)

Pimozide has a tertiary amino group as the only modifiable functional group. This can be modified with a quaternization reaction. Thus, reacting pimozide with ethyl 3-bromopropionate gives the corresponding quaternized carrier with an ester group available for further modification, in accordance with the reaction scheme shown below. This ester group can be hydrolyzed to the free acid or reduced with LAH to a primary alcohol depending on the functional group on the drug to be attached.

Exemplary Reaction Scheme 5. Quaternization of pimozide. The pendant ester group can either be hydrolyzed to the free acid or it can be reduced to the primary alcohol depending on the functional group on the drug 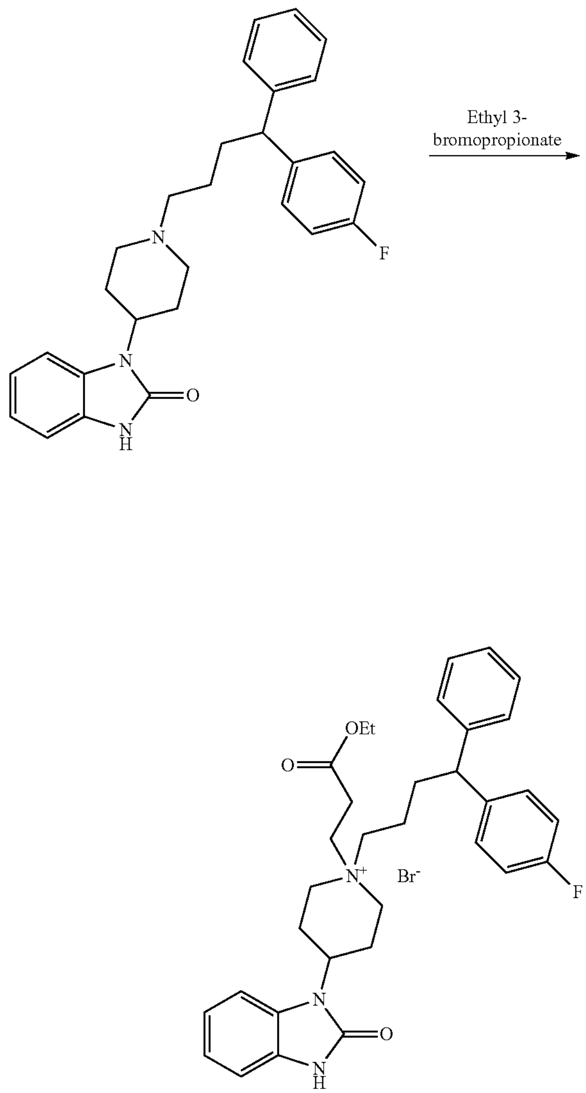 Example 6

Selected Carrier/Spacer/Drug Conjugates and Carrier/Drug Conjugates

Below are shown selected conjugates of the invention. Several conjugates are based on drug carriers and others on food substance carriers, and they show CRDCs of hydromorphone, zetia, atacand, ethinyl estradiol, norethisterone and rotigotine with carrier molecules of pimozide, tamoxifen, fluoxetine, linoleic acid, zeaxanthin, eicosapentaenoic acid (omega 6 fatty acid) and chloroquine. It is obvious to the expert in the art, that CRDCs of many different drugs can be prepared using the same strategies.

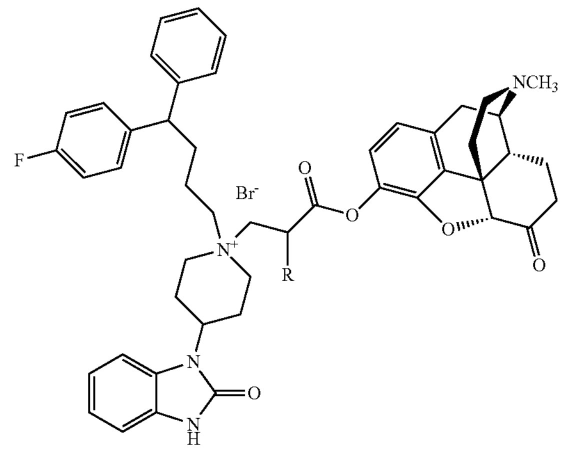

Primozide-Spacer-Hydromorphone

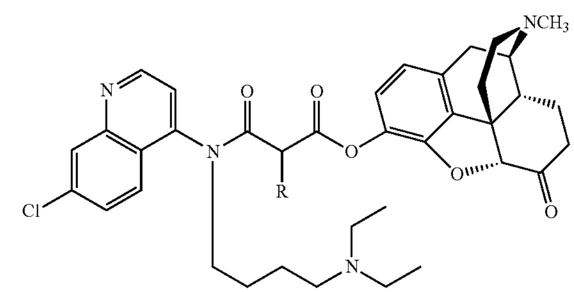

Chloroquine-spacer-Hyromorphone

R = Cl, OMe, Me, Et, IPr, etc

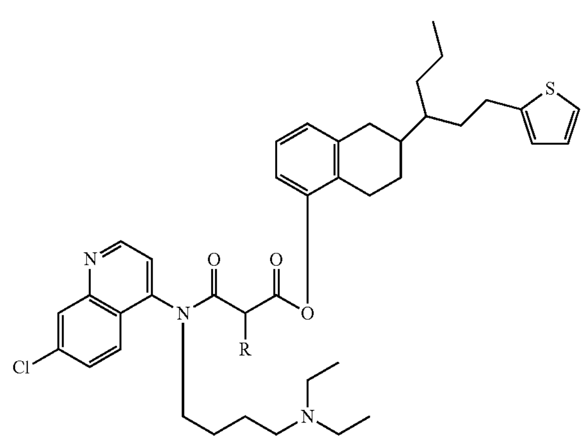

Chloroquine-Spacer-Rotigotine

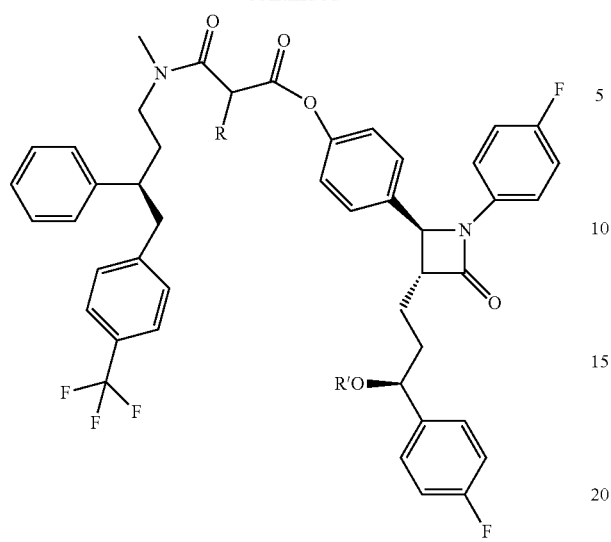

R' = H, acyl protecting group;
Fluoxetine ($t_{1/2}$ = 53 h) conjugated to Zetia via a spacer. Zetia may also be functionalized at the secondary OH group (benzylic), instead of the phenolic group (i.e. instead of R')

The following reaction schemes and exemplary conjugates utilize food substances such as zeaxanthin ($t_{1/2}$=38 days) or essential fatty acids (EFA) such as linoleic acid ($t_{1/2}$=1 day) or eicosapentaenic acid (omega 6 $t_{1/2}$=1.63 to 3.27 days) as drug carriers. In the exemplary conjugates shown below, the drug molecules are directly attached to the carrier molecules via an ester bond. Depending on the release rate desired appropriate spacers can be added to prepare full CRDCs as discussed in several of the examples and schemes presented above.

Exemplary Reaction Scheme 6a. Conjugate if zeaxanthin with two molecules of atacand

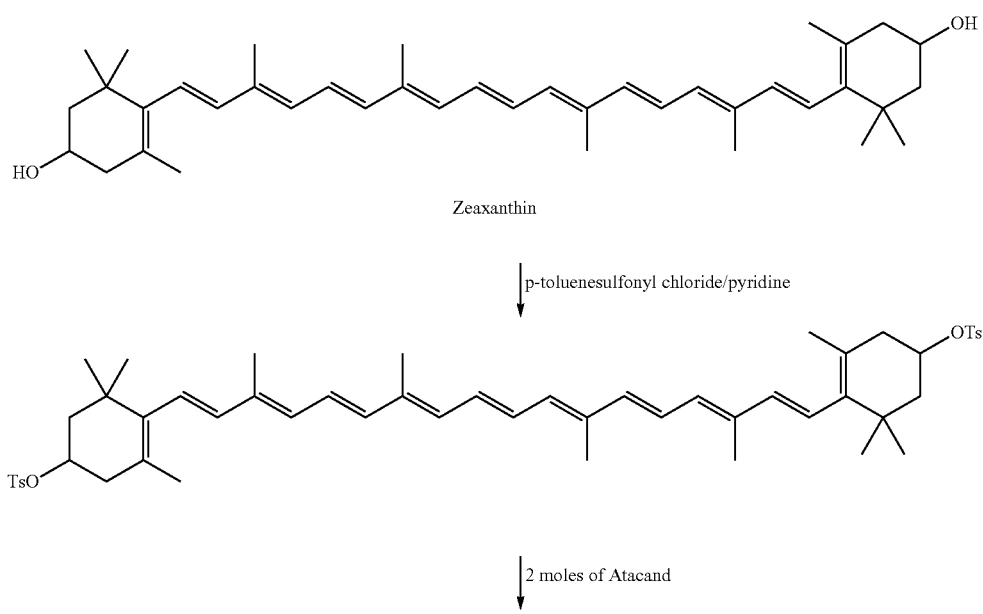

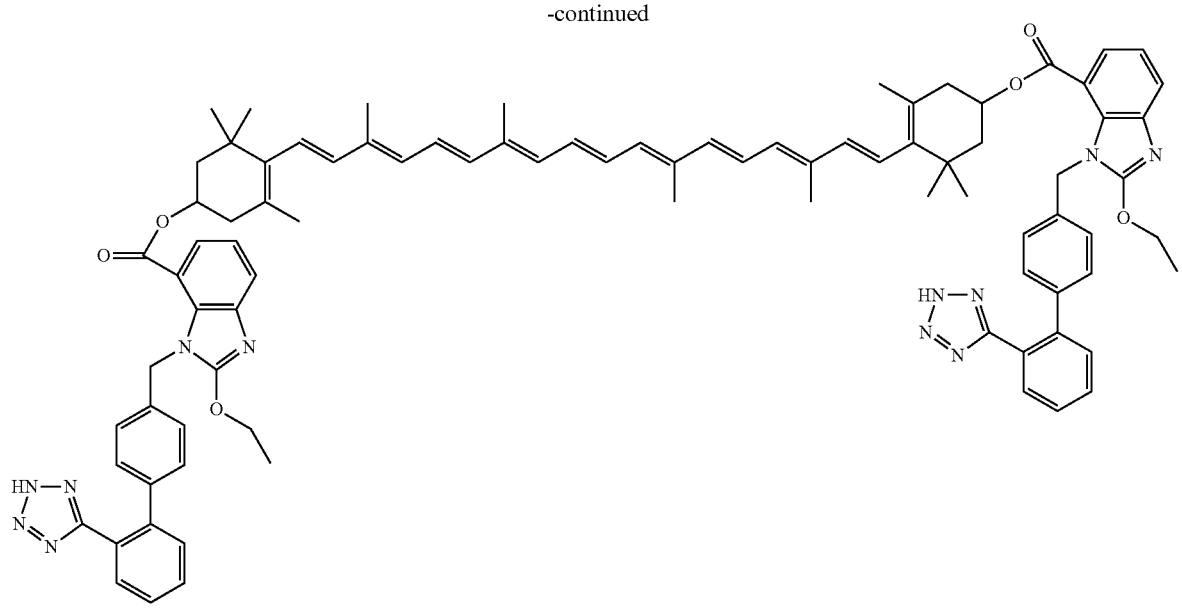

25

In the scheme above, both hydroxy groups of zeaxanthin are functionalized. This may reduce the half life of the conjugate. In the conjugate shown in the scheme below, only one of the hydroxy group is conjugated to atacand and the second one is free.

Exemplary Reaction Scheme 6b. Conjugate of zeaxanthin with one molecule of atacand. The second hydroxy group on zeaxanthin is free

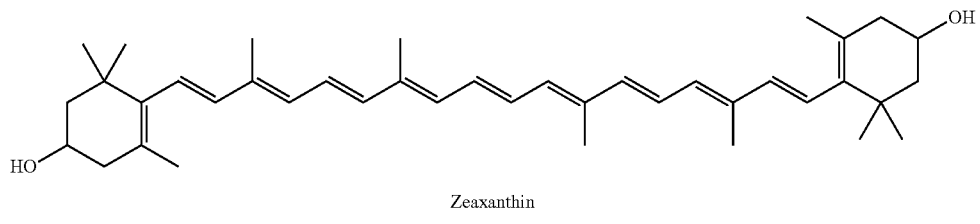

Zeaxanthin 1. p-toluenesulfonyl chloride/pyridine (1 eq)
2. Remove difunctional molecules

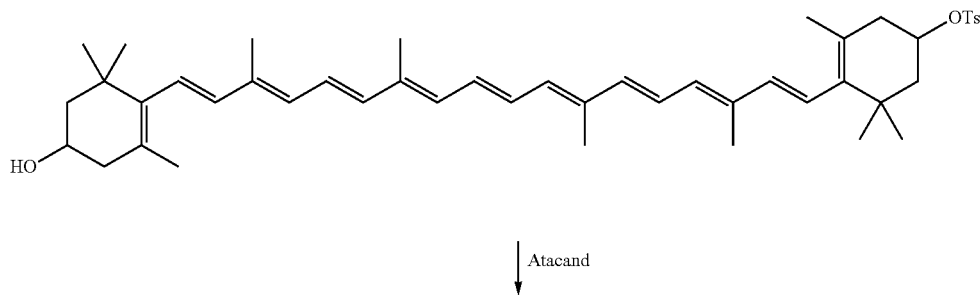

Atacand

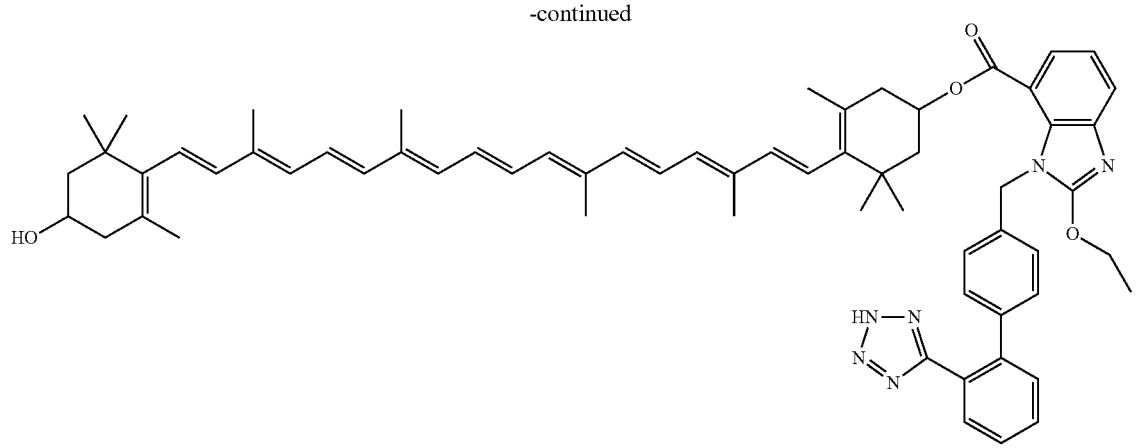
Exemplary Reaction Scheme 6c. Conjugate of Linoleic acid with Zetia. Similar conjugates can be, for example, prepared with Crestor and Lipitor
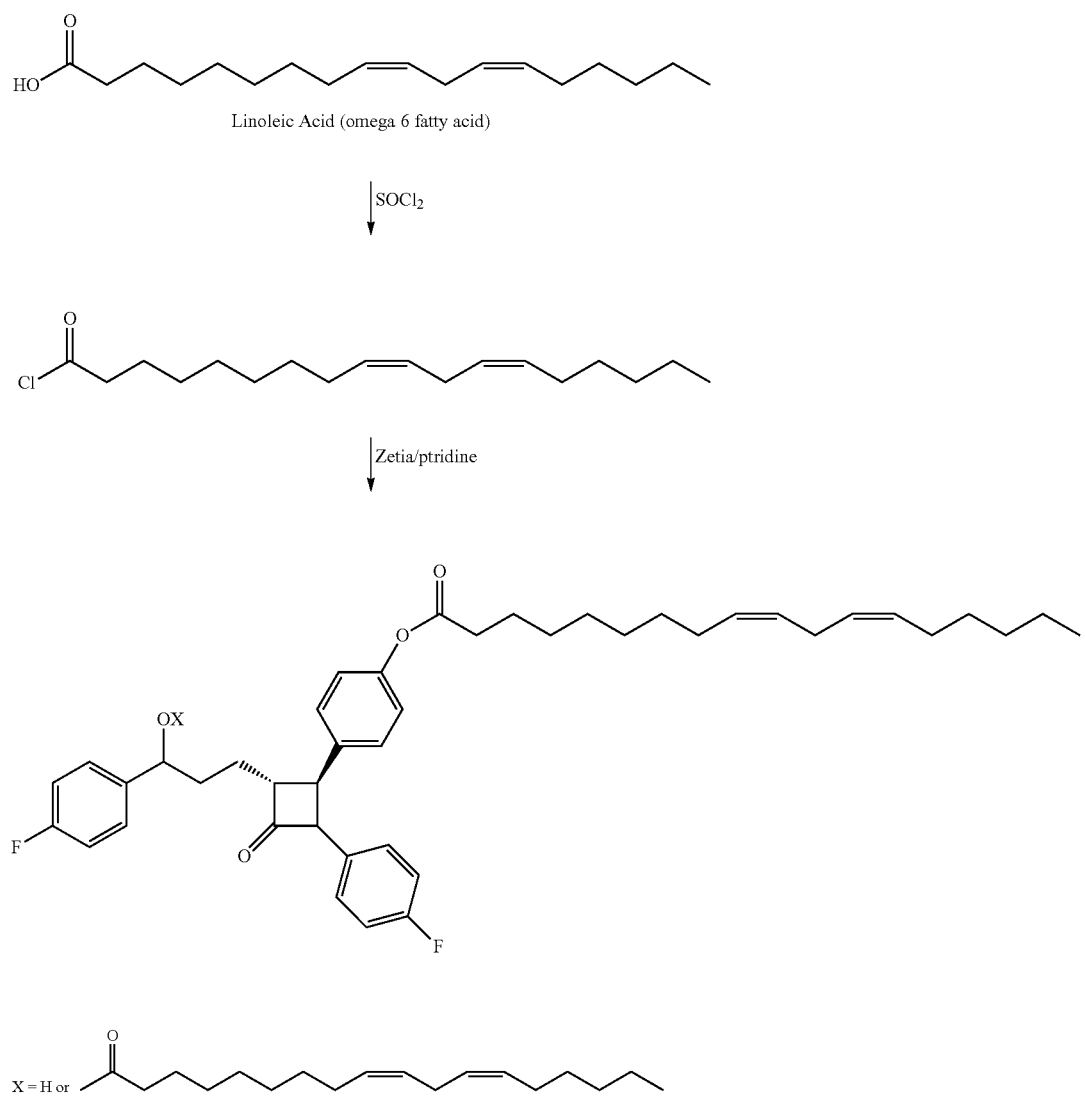

Similarly, eicosapentaenoic acid is conjugated with ethinyl estradiol, an oral hormone used in post menopausal syndrome and contraceptive formulations. Ethinyl estradiol is especially useful with my invention since it is effective in a very small dosage (50 mcgs/day or less).

Exemplary Reaction Scheme 6d. Conjugation of Ethinyl Estradiol (EE, dosage 50 mcgs/day or less) with the EFA eicosapentaenoic acid (t ½ = 67 hours). If desired a spacer can be used between the drug and the carrier molecule for fine tuning the release rate

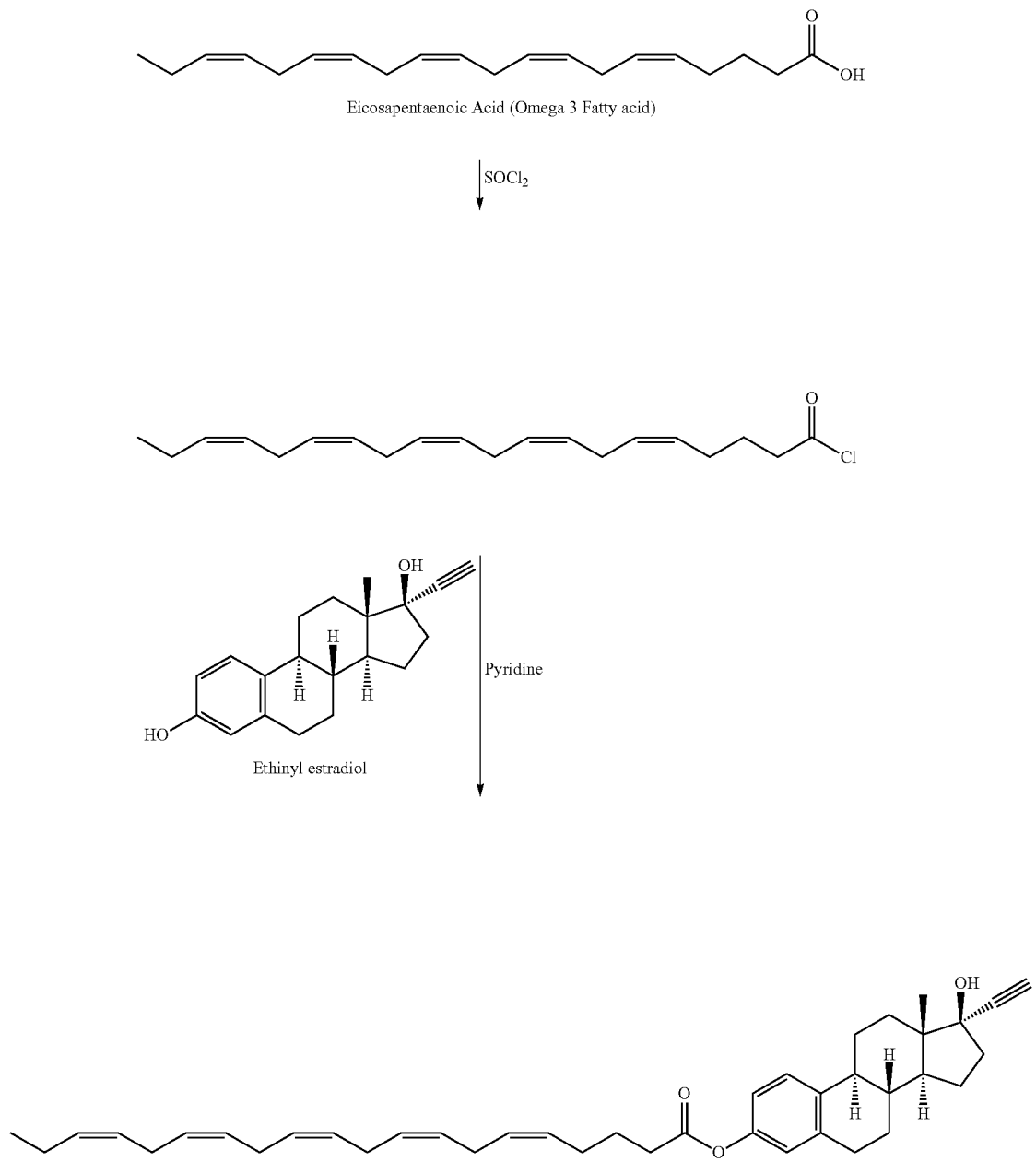

Ethinyl estradiol and other hormones such as the progestins norethisterone, desogestrel and levonorgestrel can also be conjugated with tamoxifen ($t_{1/2}$=4 to 11 days) or chloroquine ($t_{1/2}$=41 days) to obtain CRDCs with prolonged half lives. The conjugates shown below can be synthesized using the reactions described in the examples above and other standard reactions.

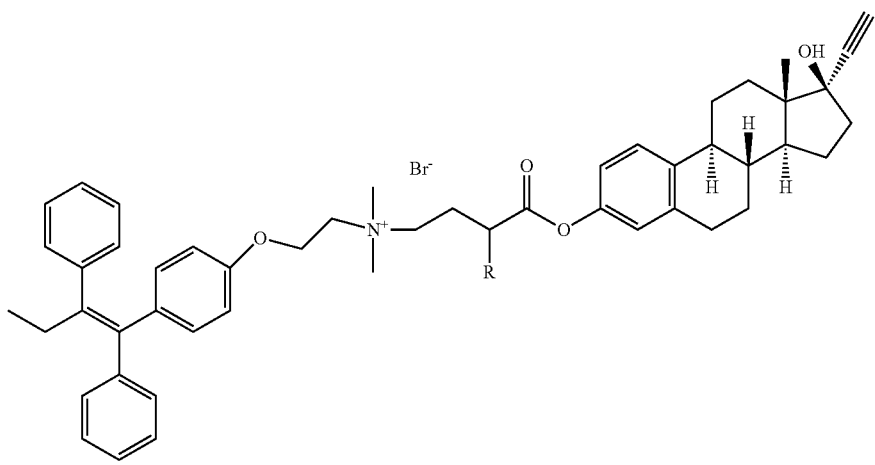

Tamoxifen-spacer-Ethinyl Estradiol

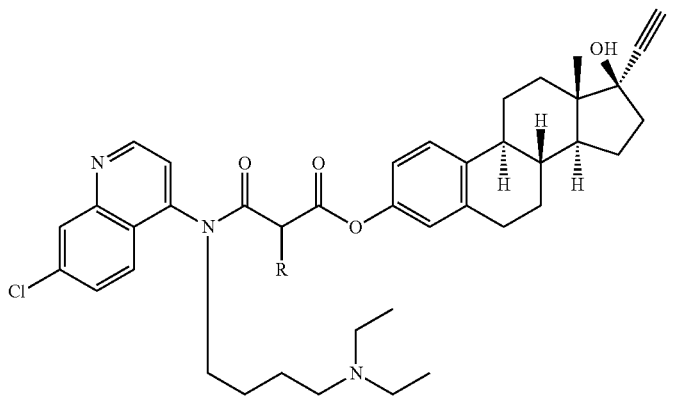

Chloroquine-Spacer-Ethinyl Estradiol

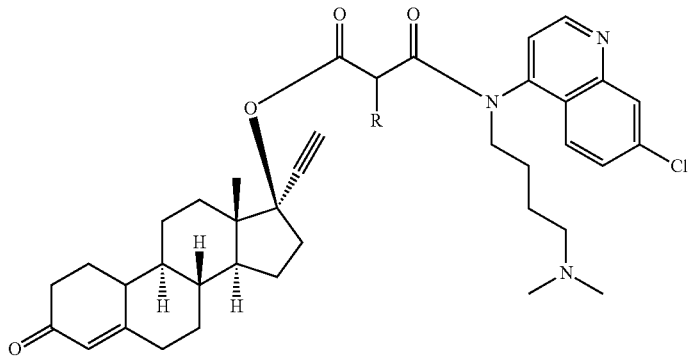

Conjugate of Norethisterone with Chloroquine via spacer

CRDC prepared by conjugating norethisterone with chloroquine via a spacer. Desogestrel and levonorgestrel can also be conjugated to chloroquine or other carrier molecules to produce CRDCs

Example 7

Production of a Dosage Form

The different schemes and examples set forth herein show how to produce controlled release drug conjugates (CRDCs). These conjugates may be direct conjugates, which is those where the carrier or carriers are directly attached to the drug or drugs. In schemes 1 through 5 of the description of illustrative embodiments, the preparation of various drug carriers with spacers for the formation CRDCs with tunable release rates is shown. I have also shown how to produce full conjugates, which is those that attach the carrier or carriers to drug or drugs through one or more spacers. I have also shown how the release of the drug from the conjugate can be controlled by the moiety of the R group on the spacer molecule, as shown in scheme 3b and Tables 1 and 2.

Therefore, in general the production of a dosage form for a specific drug X comprises the following steps:

a) Choose one or more carriers with different half lives and react to drug X directly or through one or more spacers to form direct CRDCs and/or full CRDCs of drug X.

b) Choose one or more of the above mentioned CRDCs which when hydrolyzed under physiological conditions will give the desired release profile of drug X, for the desired length of drug delivery.

c) Optionally, prepare controlled release formulations of the CRDCs, such as liposomes, nanoparticles, micelles, bioresorbable and non-resorbable polymers and other well known controlled release technologies.

d) Optionally, include a standard immediate release formulation or a standard extended release formulation, so as to rapidly bring the blood plasma concentration of drug X to the efficacious range. This may be required for only the first dosage administered to a patient.

e) Place the chosen preparation or preparations from a, b, c and d above into a capsule or formulate into a tablet to form an oral dosage form. If the administration is, for example, for injection, or for needle free injection, or for microneedle transdermal delivery, then the dosage can be formulated into an appropriate solution, emulsion or dispersion.

The exact amounts released and times of release of drug X will, of course, be dependent on the requirements for therapeutic efficacy of drug X and will need to be determined by experimentation and modifications made as needed.

It is significant to note, that the use of several carriers and spacers could be advantageous, because it minimizes the amount of each carrier and spacer molecule used and consequently any potential side effects from anyone of these molecules.

Example 8

Production of a Seven Day Dosage Form of My Invention

A single oral dose that would last for seven days is very important due to ease of usage and patient compliance. Such a dosage can be obtained by using, for example, a full CRDC where the carrier has, for example, a half life of 30 to 50 days and a spacer is chosen with the appropriate substituents on the alcohol and acid portions of the ester as to hydrolyze and provide at steady state:

a) a maximum plasma concentration at any time during the seven day period of not more than $$C_{ss,max} = F \cdot dose/V_{ss}/(1-\exp(-kT))$$

where Css,max represents the highest allowable drug in the plasma (i.e., above which results in an unacceptable side effect profile), F is the oral bioavailability, Vss is the volume of distribution at steady state, k is the rate constant for elimination that reflects the fraction of drug removed per unit time and T is the dosing interval; and b) a blood plasma concentration, at any time during the seven day period which is above $$C_{ss,min} = C_{ss,max} \cdot \exp(-kT)$$

where Css-min represents the minimum effective amount of drug in the plasma (below which the drug effectiveness is compromised) (see, e.g., The Pharmacological Basis of Therapeutics, tenth edition, McGraw-Hill, p. 26, 2001)

Css-max and Css-min are well known for each marketed drug.

The above is demonstrated in examples and 18 and 19 where the pharmacokinetics of ethinyl estradiol are shown, based on actual release data obtained from a CRDC prepared as shown in Example 15 and the release of ethinyl estradiol obtained from that conjugate, as shown in Example 17.

Example 9

Combination CRDC and Standard Release Formulations

A dosage form comprising the above mentioned CRDC (Example 8) together with a standard immediate release or a standard extended release formulation can be prepared to provide the initial rapid release required. It is understood from the above descriptions that dosage forms for two day delivery or three and a half day delivery can be similarly obtained.

Example 10

Seven Day Preparation for Ovulation Suppression

Ovulation suppression for prevention of pregnancies is a multibillion dollar worldwide market. Drugs used for that purpose are combinations of progestins and estrogens. Levonorgestrel and ethinyl estradiol are very commonly used for this purpose. The daily dosage of each drug required for effectiveness is very small, which is a preferred embodiment of the present invention. The plasma concentrations of ethinyl estradiol are only 20 to 50 picograms per ml and for levonorgestrel about 1 microgram per ml. I have shown in Example 6 and the exemplary reaction schemes set forth therein CRDCs of ethinyl estradiol with and without spacers, as well as a CRDC of a progestin with a spacer. These CRDCs and others can be used to prepare dosage forms delivering the required amounts of levonorgestrel and ethinyl estradiol for a seven day delivery period from a single administration of a dosage form comprising the CRDCs of the present invention.

Example 11

Suppresion of Post Menopausal Symptoms

Ethinyl estradiol as well as 17-beta estradiol are used as monotherapy for hormone replacement therapy, to prevent post menopausal symptoms. The dosage required is similar to the one mentioned above. Therefore the CRDCs described in Example 6 and modifications thereof can be used to provide seven day hormone replacement therapy from a single administration of a dosage form comprising the CRDCs of the invention.

Example 12

Seven Day Antihypertensive Treatment

Only 27.6% of antihypertensive patients in the United States have adequate blood pressure control even though there are over 100 medications available (Arch. Inten. Med. 175 (21): 2413, 1997; Hypertension 26:60 1995). This inadequate blood pressure control is due to lack of patient compliance and convenience of dosing schedule. For example, studies have shown that after one year, only 30% of patients are still taking their antihypertensive medication (Hypertension Medicine, Humana Press, Totowa, N.J. p. 232). Dosing schedules have also been shown to be critically important in blood pressure control with, for example, drugs dosed twice daily taken less frequently than other drugs (Drugs 48:16, 1994) and (N. Eng. J. Med 313:1315 1985).

Several classes of antihypertensive drugs can be modified in accordance with the present invention, including beta blockers, diuretics, calcium channel blockers, ACE inhibitors and angiotensin II receptor blockers (ARB). Example 6 shows exemplary CRDCs of atacand, an ARB, which together with other CRDCs of atacand can be used to produce 7 day control of hypertension, from a single administration of a dosage form comprising the CRDCs of the invention.

Example 13

Control of Blood Cholesterol

Zetia, lipitor, crestor and several other lipid lowering compounds are used extensively to reduce the cholesterol levels in the blood and thus reduce cardiovascular events such as heart attacks and strokes. In fact, the lipid lowering market is the largest dollar volume category among all drug categories, accounting for more than 10 billion dollar sales per year. Example 6 sets forth examples of direct as well as full CRDCs of Zetia. These CRDCs and others which can be easily produced as described in the schemes and examples mentioned above can be used to produce seven day control of blood cholesterol, from a single administration of a dosage form comprising the CRDCs of the invention.

Example 14

Preparation of Mefloquine Succinate (Attachment of Spacer to Carrier Molecule)

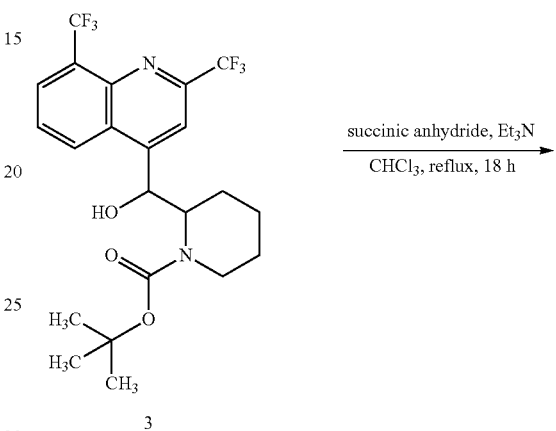

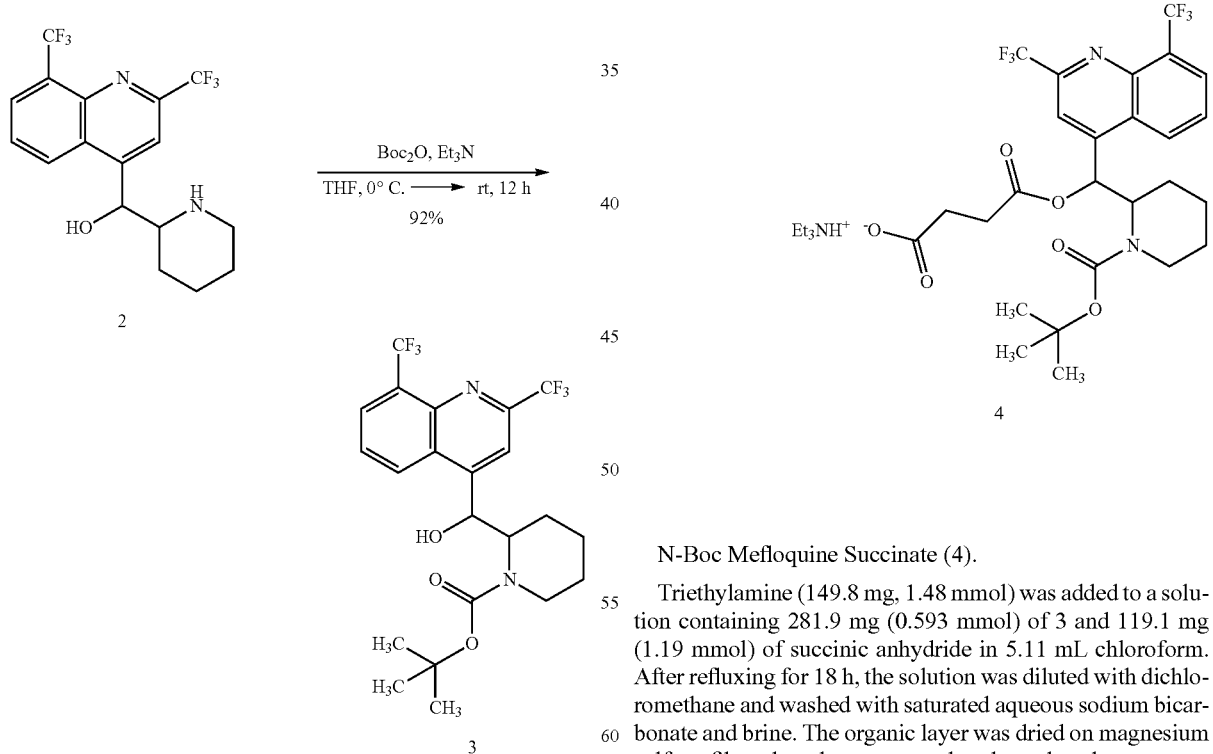

N-Boc Mefloquine (3).

Mefloquine (249.5 mg, 0.665 mmol) was dissolved in 3.33 mL of distilled THF, and the solution was cooled in a 0° C. ice bath. Di-tert-butyl dicarbonate (217.8 mg, 0.998 mmol) and triethylamine (168.0 mg, 1.66 mmol) was added to the cooled solution. After stirring at room temperature for 12 h, the mixture was washed with water and brine, dried on magnesium sulfate, and then concentrated under reduced pressure. Silica gel column chromatography using 1:4 ethyl acetate/hexanes as the eluent afforded 292 mg of 3 in 92% yield: $^1$H NMR (500 MHz, CDCl$_3$) δ 8.65 (d, J=8.5 Hz, 1H), 8.17 (d, J=7.0 Hz, 1H), 8.04 (s, 1H), 7.76 (t, J=8.0 Hz, 1H), 5.83 (t, J=4.0 Hz, 1H), 4.29 (q, J=5.5 Hz, 1H), 3.82 (br d, J=13.0 Hz, 1H), 3.24 (ddd, J=4.0, 10.5, 14.5 Hz, 1H), 3.15 (br s, 1H), 1.73-1.95 (m, 2H), 1.34-1.66 (m, 4H), 1.32 (s, 9H); ESI-MS m/z 501 MNa$^+$.

N-Boc Mefloquine Succinate (4).

Triethylamine (149.8 mg, 1.48 mmol) was added to a solution containing 281.9 mg (0.593 mmol) of 3 and 119.1 mg (1.19 mmol) of succinic anhydride in 5.11 mL chloroform. After refluxing for 18 h, the solution was diluted with dichloromethane and washed with saturated aqueous sodium bicarbonate and brine. The organic layer was dried on magnesium sulfate, filtered, and concentrated under reduced pressure to give 340 mg of 4 as light-brown oil, which was carried to the next step without further purification: $^1$H NMR (500 MHz, CDCl$_3$) δ 12.46 (br s, 1H), 8.71 (br s, 1H), 8.13 (d, J=7.0 Hz, 1H), 7.85 (s, 1H), 7.76 (t, J=8.0 Hz, 1H), 6.68 (br s, 1H), 4.74 (br s, 1H), 3.95 (br s, 1H), 2.93 (dt, J=13.0, 3.0, 1H), 2.87 (q, J=7.5, 6H), 2.66 (t, J=7.0 Hz, 2H), 2.51 (t, J=7.0, 2H), 1.97 (br s, 1H), 1.34-1.80 (m, 5H), 1.09 (t, J=7.5 Hz, 9H), 1.04 (br s, 9H); ESI-MS m/z 601 MNa$^+$, 577 M.

Example 15

Preparation of Mefloquine-Succinate-Ethinyl Estradiol Conjugate (Attachment of Drug to Carrier-Spacer Conjugate)

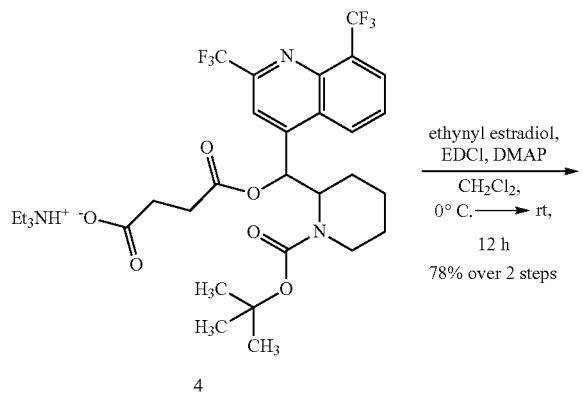

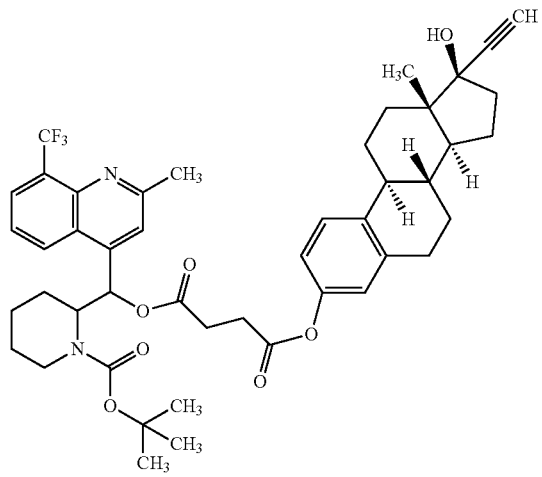

Estradiol Ester 1.

Succinate 4 (43.8 mg, 0.065 mmol) was dissolved in 0.65 mL dichloromethane, and the solution was cooled in a 0° C. ice bath. Ethinyl estradiol (21.0 mg, 0.071 mmol) was added to the cooled solution, followed by 13.6 mg (0.071 mmol) of N-(3-diethylaminopropyl)-N'-ethylcarbodiimide hydrochloride) and 1.6 mg (0.013 mmol) of DMAP. After 12 h of stirring at room temperature, the reaction was washed with water and brine, concentrated, and chromatographed on silica gel using 3:7 ethyl acetate/hexanes as eluent, affording 53 mg of 1 as a white powder (78% yield over 2 steps): NMR (500 MHz, CDCl$_3$) δ 8.71 (br s, 1H), 8.17 (d, J=7.5 Hz, 1H), 7.86 (s, 1H), 7.79 (t, J=8.0 Hz, 1H), 7.24 (d, J=8.5 Hz, 1H), 6.80 (br d, J=3.0 Hz, 1H), 6.73 (dt, J=8.5, 3.0 Hz, 1H) 6.68 (d, J=2.0 Hz, 1H), 4.79 (br s, 1H), 3.97 (br s, 1H), 2.74-2.98 (m, 7H), 2.61 (s, 1H), 2.20-2.40 (m, 3H), 1.62-2.06 (m, 10H), 1.30-1.58 (m, 7H), 1.09 (br s, 9H), 0.88 (s, 3H): ESI-MS m/z 879 MNa$^+$.

Example 16

Preparation of a Second Conjugate of Ethinyl estradiol by Removal of the t-butyloxycarbonyl Group from Conjugate 1 of Example 15

The chemical reaction in removing the t-butyloxycarbonyl group is shown below. Since the amine group is no longer blocked, the new conjugate would have higher solubility in water and release the ethinyl estradiol at different rate than the conjugate 1 of Example 15. A third conjugate can also be prepared by simply migrating the spacer and ethinyl estradiol to the amino group and freeing the OH group.

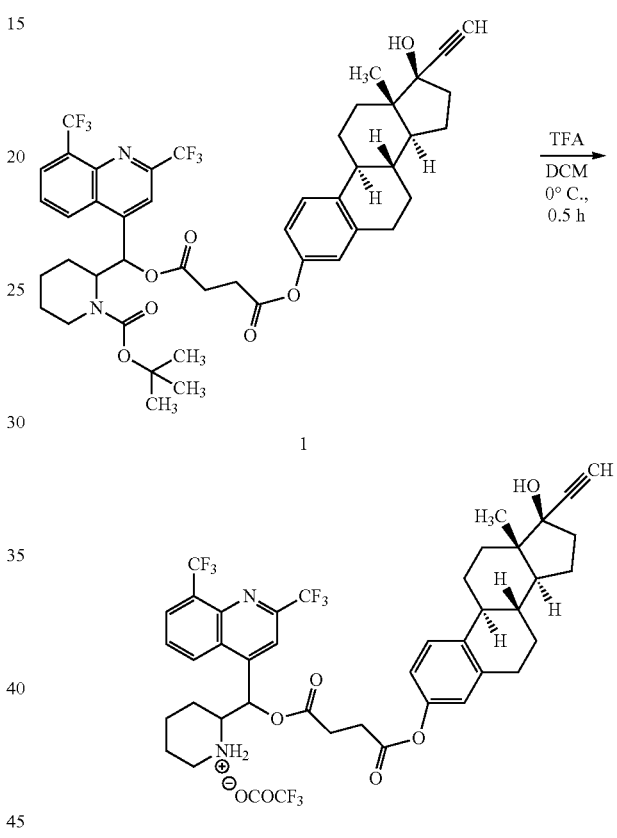

Removal of t-Butyloxycarbonyl Group from 1.

Ester 1 (9.8 mg, 0.011 mmol) was dissolved in 0.11 mL dichloromethane, and the solution was cooled in a 0° C. ice bath. Trifluoroacetic acid (104 mg, 0.915 mmol) was added to the cooled solution. After 0.5 h of stirring at 0° C., the reaction was concentrated, then concentrated twice more from toluene to produce 11.1 mg of crude 1 as a white powder: $^1$H NMR (500 MHz, CDCl$_3$) δ 10.23 (br s, 1H), 9.77 (br s, 1H), 8.87 (d, J=8.5 Hz, 1H), 8.26 (d, J=7.0 Hz, 1H), 7.91 (t, J=8.0 Hz, 1H), 7.87 (s, 1H), 7.28 (br s, 1H), 7.18 (t, J=9.0 Hz, 1H), 6.73 (ddd, J=2.5, 4.5, 7.5 Hz, 1H), 6.66 (br s, 1H), 3.72 (d, J=12 Hz, 1H), 3.38 (br s, 1H), 3.14 (dt, J=6.0, 17.5 Hz, 1H), 3.01 (dt, J=7.0, 18 Hz, 1H), 2.70-2.92 (m, 5H), 2.59 (s, 1H), 2.14-2.28 (m, 3H), 1.62-2.08 (m, 10H), 1.12-1.58 (m, 7H), 0.83 (d, J=3.5 Hz, 3H); ESI-MS m/z 757 MH$^+$.

Example 17

Hydrolysis of Ethinyl Estradiol (EE) from the Conjugate

Estradiol conjugate 1 (23.0 mg, 0.027 mmol) was dissolved in 48 mL of a 2:1 ethanol/0.05 M aqueous phosphate buffer (pH 7.4) mixture, and the solution was shaken in a 37° C. incubator for 6 days. Estradiol release was determined by integration of $^1$H NMR signals obtained from three 8.5 mL aliquots, which were collected at 2-, 3-, and 6-day intervals. Results are shown in Table 3.

TABLE 3

| Day | Ethinyl Estradiol Released (%) |
|---|---|
| 2 | 57 |
| 3 | 67 |
| 6 | 100 |

The results demonstrate that ethinyl estradiol is released from conjugate 1 over a several day period.

Example 18

Calculation of Pharmacokinetic Profile of Orally Delivered 3/1;2 Day or 7 Day Pill using the Data of Example 17

Figure 1B:
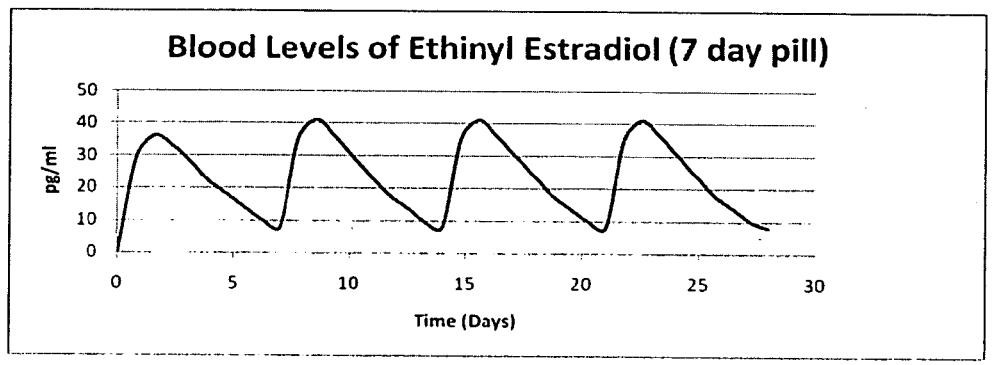

Since the release of EE is from a non-constant activity source, i.e., the concentration of the conjugate is continuously decreasing, the release of EE from the conjugate will obey a first order release and thus be proportional to the concentration of conjugate at any time t. These equations have been solved and the final equation describing the release of the EE is given by the equation Mt/M0=1−1/exp(kt), where Mt is the amount of EE released from the conjugate, M0 is the total amount of EE, Mt/M0 is the percent EE released from the conjugate, k is a proportionality constant and t is the time. The constant k was calculated from the data shown in example 17 to be 0.42. From this equation, the amounts of EE released at any time point can be calculated and the pharmacokinetic profile (picograms of EE per ml of blood versus time) can be calculated using the Clearance (CL) and Oral Bioavailability (F) for EE (CL/F=486 ml/hr/kg; half life taken as 18.7 hours; Physicians Desk Reference p. 3372, 57 ed., 2003). The pharmacokinetic profiles obtained using pills containing 150 (7 day pill) and 110 (3½ day pill) microgram equivalents of EE are shown in FIG. 1A and FIG. 1B. From these figures it is indicated that the above experimental data supports a regimen of taking a pill once every 3½ days, with peak to valley ratios (Css.max to Css.min) of less than two. It is not apparent that the data of experiment 17 will suggest a regimen of 1 pill taken every 7 days for many drugs, as the peak to valley ratios are large (peak to valley ratio 5.1).

Example 19

Calculation of Pharmacokinetic Profile of Orally Delivered 3½ Day or 7 Day Pill using a Conjugate with Approximately Half the Rate of Release of EE, as that of Conjugate of Example 17

Figure 2A:
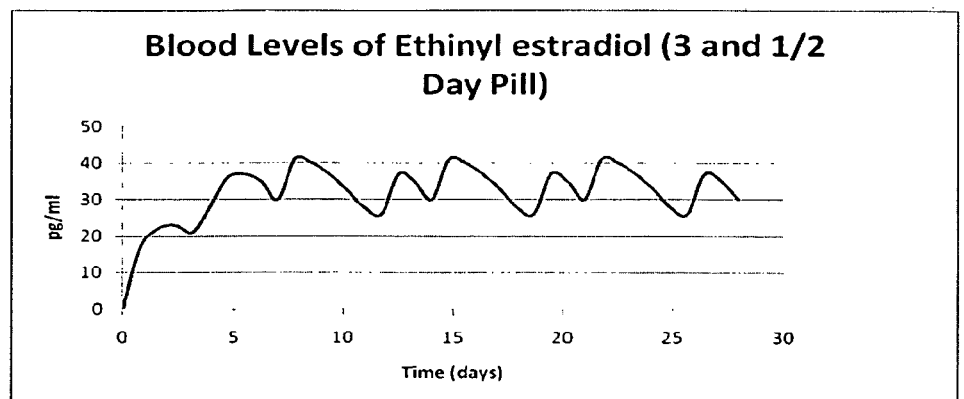
FIG. 2. Graphs showing predicted pharmacokinetic profile of orally delivered 3.5 day (FIG. 2A) or 7 day (FIG. 2B) calculated for a conjugate having half the hydrolysis rate of conjugate 1 (mefloquine-succinate-ethinyl estradiol).
Figure 2B:
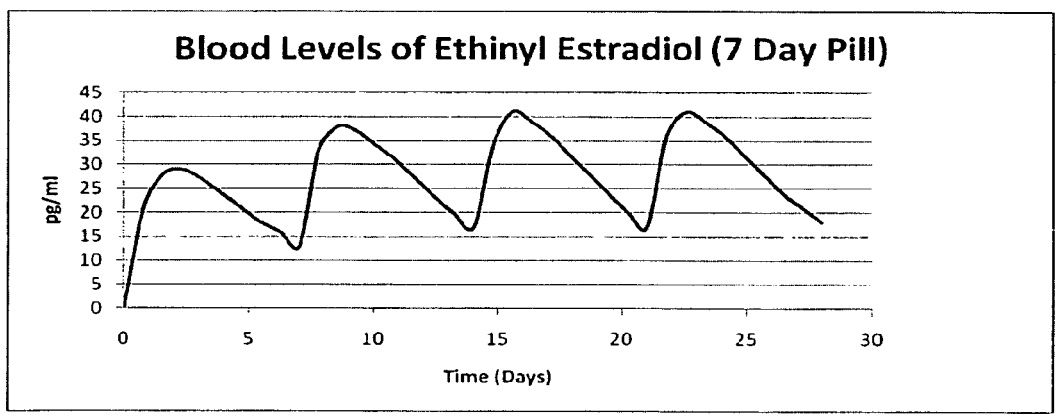

As was shown in Example 18, the release from the EE conjugate is governed by the equation Mt/M0=1−1/exp(kt). The value of k was 0.42 as determined from the data of example 17. As discussed in the detailed description of illustrative embodiments, the release can be controlled by many different factors. To obtain half the release rate of EE as compared with that of conjugate of example 17, a value of k=0.22 was used. Using k=0.22 and the pharmacokinetic parameters shown in Example 18, the graphs shown in FIG. 2A and FIG. 2B were obtained. It is significant to note that both the 3½ day pill as well as the 7 day pill delivered blood levels that would be appropriate for most drugs, with peak to trough ratios of 1.4 and 2.3 respectively. The conjugates used in the 3½ day and the 7 day pills contained 148 and 188 micrograms of EE respectively.

Example 20

Hydrolysis of Ethinyl Estradiol (EE) from Conjugate of Example 16

Estradiol conjugate (33.5 mg, 0.039 mmol), prepared from Conjugate 1 as described in Example 16, was dissolved in 58 mL of a 9:4 ethanol/0.05 M aqueous phosphate buffer (pH 7.4) mixture, and the solution was shaken in a 37° C. incubator for 9 days. Six 8 mL aliquots were collected at 1-, 2-, 3-, 5-, 7-, and 9-day intervals. Estradiol release was quantified by adding 33 µL of a 0.09 M solution of butylated hydroxytoluene (BHT) in deuterochloroform as an internal standard, then comparing integrals of 1H NMR signals corresponding to the steroid and the internal standard. Results are shown in Table 4 below.

TABLE 4

| Day | Ethinyl Estradiol Released (%) |
|---|---|
| 1 | 30 |
| 2 | 50 |
| 3 | 63 |
| 5 | 77 |
| 7 | 88 |
| 9 | 98 |

As can be seen from the table, the rate of hydrolysis from this conjugate appears to be slower than that of Conjugate 1 (examples 15 and 17). This reduction rate of drug release was accomplished by reacting the spacer on a different reaction site of the carrier molecule.

The present invention is not limited to the embodiments described and exemplified above, but is capable of variation and modification within the scope of the appended claims.

What is claimed:

1. An oral pharmaceutical dosage form comprising a drug linked to a carrier by a spacer, wherein: (1) the drug is hydromorphone, zetia, lipitor, crestor, atacand, ethinyl estradiol, 17 beta-estradiol, levonorgestrel, norgestimate, norethisterone and rotigotine; (2) the carrier is pimozide, tamoxifen, fluoxetine, linoleic acid, zeaxanthin, eicosapentaenoic acid, chloroquine, or hydroxychloroquine; and (3) the spacer is hydrolyzable or enzymatically cleavable in the gastrointestinal tract of a patient ingesting the dosage form.

2. The oral dosage form of claim 1, wherein the carrier has a half life in a patient's body of more than one day.

3. The oral dosage form of claim 1, wherein the drug is released from the carrier in the gastrointestinal tract of the patient's body.

4. The oral dosage form of claim 1, wherein the spacer increases or decreases the half life of the oral dosage form conjugate, as compared with an equivalent oral dosage form conjugate prepared without the spacer.

5. The oral dosage form of claim 1, wherein the spacer comprises one or more diols, diamines, diacids, aminoacids, aminoalcohols, hydroxyacids, dithiols, hydroxythiols, aminothiols, mercaptocarboxylates, dialkylsulfates, phosphate diesters, and phosphate triesters.

6. The oral dosage form of claim 5, wherein the spacer comprises citric acid, tartaric acid succinic acid, glutaric acid, glycine, polyethylene glycol or modified polyethylene glycol.

7. The oral dosage form of claim 1, selected from: linoleic acid linked to zetia, crestor or Lipitor, and eicosopentaenoic acid, tamoxifen or chloroquine linked to ethinyl estradiol.

8. The oral dosage form of claim 1, comprising a daily dosage of less than about 100 milligrams of the drug.

9. The oral dosage form of claim 1, further comprising the drug not linked to the carrier and, optionally, one or more excipients for facilitating controlled release of the drug not linked to the carrier.

10. The oral dosage form of claim 1, further comprising one or more other active agents.

\* \* \* \* \*